United States Patent [19]

Küfner-Mühl et al.

[11] Patent Number: 5,719,279
[45] Date of Patent: Feb. 17, 1998

[54] ASYMMETRICALLY SUBSTITUTED XANTHINES

[75] Inventors: Ulrike Küfner-Mühl, Ingelheim; Helmut Ensinger, Ingelheim am Rhein; Joachim Mierau, Mainz; Franz Josef Kuhn, Gau-Algesheim; Erich Lehr, Waldalgesheim; Enzio Müller, Bingen/Rh., all of Germany

[73] Assignee: Boehringer Ingelheim KG, Ingelheim am Rhein, Germany

[21] Appl. No.: 661,567

[22] Filed: Jun. 11, 1996

Related U.S. Application Data

[63] Continuation of Ser. No. 329,020, Oct. 25, 1994, abandoned, which is a continuation of Ser. No. 104,831, Aug. 10, 1993, abandoned.

[30] Foreign Application Priority Data

Aug. 10, 1992 [DE] Germany .......................... 42 26 371.9
Nov. 13, 1992 [DE] Germany .......................... 42 38 423.0

[51] Int. Cl.$^6$ ............ C07D 473/10; C07D 473/06; C07D 247/02; A61K 31/52
[52] U.S. Cl. ............ 544/61; 544/118; 544/269; 544/270; 544/271; 544/272; 544/273
[58] Field of Search ............................... 544/264, 270, 544/271, 272, 61, 118, 273

[56] References Cited

U.S. PATENT DOCUMENTS 5,366,977  11/1994  Pollard ........................ 514/263

FOREIGN PATENT DOCUMENTS 94-03456  2/1994  WIPO .

OTHER PUBLICATIONS

Mueller, J Med Chem 36,3341 (1993).
Jacobson, J Med Chem 35,407 (1992).
Patel, Mol Pharma 33,585 (1988).

*Primary Examiner*—Mark L. Berch
*Attorney, Agent, or Firm*—R. P. Raymond; M-E. M. Devlin; A. R. Stempel

[57] ABSTRACT

Xanthine derivatives of formula

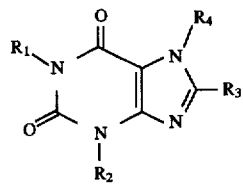

wherein $R_1$ is hydrogen, alkyl or alkynyl, $R_2$ is different and is alkyl, alkynyl, phenyl-alkylene, phenyl alkenylene, cycloalkyl, inter alia, $R_3$ is cycloalkyl, phenyl, norbornane, inter alia and $R_4$ is hydrogen, methyl, benzyl, inter alia.

9 Claims, No Drawings

ASYMMETRICALLY SUBSTITUTED XANTHINES

This is a continuation, of application Ser. No. 08/329,020, filed Oct. 25, 1994, abandoned which is a continuation of application Ser. No. 08/104,831, filed Aug. 10, 1993 abandoned.

The present invention relates to new xanthine derivatives, processes for preparing them and their use as pharmaceutical compositions and their use as intermediates.

The new compounds correspond to the general formula

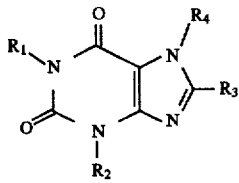

wherein $R_1$ cannot simultaneously represent $R_2$, and are defined as follows:

$R_1$ represents hydrogen, $C_1$–$C_6$-alkyl, preferably methyl, ethyl, n-butyl or allyl, most preferably n-propyl, $C_3$–$C_6$-akenyl, $C_3$–$C_6$-alkynyl;

$R_2$ denotes hydrogen, a $C_1$–$C_8$-alkyl-, $C_2$–$C_8$-alkenyl- or $C_2$–$C_8$-alkynyl- group which is substituted by —CN, —CH$_2$NR$_6$R$_7$, OH (multiple substitution also being possible), —OR$_8$, —NR$_6$R$_7$, —NHCOR$_8$, —NHCONR$_6$R$_7$, halogen, —OCOR$_8$, —OCH$_2$COOH, —OCH$_2$COOR$_8$, —OCH$_2$COOR$_8$, —SO$_2$R$_5$, —S—R$_5$, —NHCONH phenyl, —OCH$_2$—CONR$_6$R$_7$, —OCH$_2$CH$_2$OH, —SO$_2$—CH$_2$—CH$_2$—O—COR$_8$, —OCH$_2$—CH$_2$—NR$_6$R$_7$, —SO$_2$—CH$_2$—CH$_2$—OH, —CONHSO$_2$R$_8$, —CH$_2$CONHSO$_2$R$_8$, —OCH$_2$CH$_2$OR$_8$, —COOH, —COOR$_8$, —CONR$_6$R$_7$, —CHO, —SR$_8$, —SOR$_8$, —SO$_2$R$_8$, —SO$_3$H, —SO$_2$NR$_6$R$_7$, —OCH$_2$—CH$_2$OCOR$_8$, —CH=NOH, —CH=NOR$_8$, —COR$_9$, —CH(OH)R$_9$, —CH(OR$_8$)$_2$, —CH=CH—R$_{10}$, OCONR$_6$R$_7$,

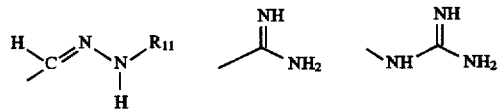

or by 1,3-dioxolane or 1,3-dioxane which is optionally mono- or polysubstituted, preferably mono- substituted, by methyl;

$R_2$ denotes phenyl-$C_1$–$C_6$-alkylene, preferably phenyl-$C_1$–$C_4$-alkylene, phenyl-$C_2$–$C_6$-alkenylene or phenyl-$C_2$–$C_6$-alkynylene, in which the phenyl ring is optionally substituted, either directly or via a $C_1$–$C_4$-alkylene group, with one or more, preferably one, of the following groups, —$C_1$–$C_3$-alkyl, —CN, —CH$_2$NR$_6$R$_7$, —NO$_2$, —OH, —OR$_8$, —CH$_2$—NH—SO$_2$—R$_8$, —NHCOR$_8$, —NHCONR$_6$R$_7$, halogen, —OCOR$_8$, —OCH$_2$COOH, —OCH$_2$COOR$_8$, —CH$_2$OCOR$_8$, —SO$_2$R$_5$, —OCH$_2$—CONR$_6$R$_7$, —OCH$_2$CH$_2$OH, —OCH$_2$—CH$_2$—NR$_6$R$_7$, —CONHSO$_2$R$_8$, —OCH$_2$CH$_2$OR$_8$, —COOH, —COOR$_8$, —CF$_3$, cyclopropyl, —CONR$_6$R$_7$, —CH$_2$OH, —CH$_2$OR$_8$, —CHO, —SR$_8$, —SOR$_8$, —SO$_2$R$_8$, —SO$_3$H, —SO$_2$NR$_6$R$_7$, —OCH$_2$—CH$_2$OCOR$_8$, —CH=NOH, —CH=NOR$_8$, —COR$_9$, —CH(OH)R$_9$, —CH(OR$_8$)$_2$, —NHCOOR$_8$, —CH$_2$CONHSO$_2$R$_8$, —CH=CH— $R_{10}$, —OCONR$_6$R$_7$, —CH$_2$—O—CONR$_6$R$_7$, —CH$_2$—CH$_2$—O—CONR$_6$R$_7$,

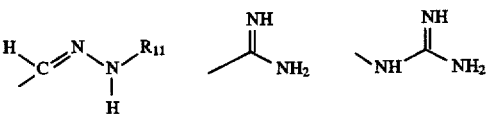

or by 1,3-dioxolane or 1,3-dioxane which is optionally mono- or polysubstituted, preferably monosubstituted, by methyl;

$R_2$ denotes $C_3$–$C_7$-cycloalkyl-$C_1$–$C_6$-alkylene-, $C_3$–$C_7$-cycloalkyl-$C_2$–$C_6$-alkenylene-, $C_3$–$C_7$-cycloalkyl-$C_2$–$C_6$-alkynylene-, in which the cycloalkyl group may optionally be substituted, either directly or via a $C_{1-4}$-alkylene group, by —CN, —CH$_2$NR$_6$R$_7$, =O, —OH, —OR$_8$, —NR$_6$R$_7$, —NHCOR$_8$, —NHCONR$_6$R$_7$, halogen, —OCOR$_8$, —OCH$_2$COOH, —OCH$_2$COOR$_8$, —CH$_2$OCOR$_8$, —SO$_2$R$_5$, —OCH$_2$CONR$_6$R$_7$, —OCH$_2$CH$_2$OH, —OCH$_2$—CH$_2$—NR$_6$R$_7$, —OCH$_2$CH$_2$OR$_8$, —COOH, —COOR$_8$, —CONR$_6$R$_7$, —CH$_2$OH, —CH$_2$OR$_8$, —CHO, —SR$_8$, —SOR$_8$, —SO$_2$R$_8$, —SO$_3$H, —SO$_2$NR$_6$R$_7$, —OCH$_2$—CH$_2$—OCOR$_8$, —CH=NOH, —CH=NOR$_8$, —COR$_9$, —CH(OH)R$_9$, —CONHSO$_2$R$_8$, —CH(OR$_8$)$_2$, —NHCOOR$_8$, —CH=CH—R$_{10}$, —OCONR$_6$R$_7$, CH$_2$—O—CONR$_6$R$_7$, —CH$_2$—CH$_2$—O—CONR$_6$R$_7$,

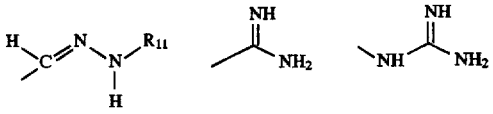

or by 1,3-dioxolane or 1,3-dioxane which is optionally mono- or polysubstituted, preferably monosubstituted, by methyl;

$R_2$ denotes a group of the formula A—$C_1$–$C_6$-alkylene-, A—CONH-$C_1$–$C_6$-alkylene-, A—CONH-$C_2$–$C_6$-alkenylene-, A—CONH-$C_2$–$C_6$-alkynylene-, A—NH—CO-$C_1$–$C_6$-alkylene, A—NH—CO-$C_2$–$C_6$-alkenylene, A—NH—CO—$C_2$–$C_6$ alkynylene, A—$C_2$–$C_6$-alkenylene- or A—$C_2$–$C_6$-alkynylene, wherein A is a C- or N-linked 5- or 6-membered heterocyclic ring which contains nitrogen, oxygen or sulphur as heteroatoms and may optionally be mono- or polysubstituted, preferably monosubstituted, by $C_1$–$C_4$-alkyl, halogen, —OR$_8$, —CN, —NO$_2$, —NH$_2$, —CH$_2$NR$_6$R$_7$, —OH, =O, a ketal, —COOH, —SO$_3$H, —COOR$_8$, —CONR$_6$R$_7$, —COR$_9$, —SO$_2$—R$_8$, —CONR$_6$R$_7$ or

$R_3$ denotes $C_3$–$C_7$-cycloalkyl, preferably cyclopentyl, optionally substituted by =O, —OH, —OR$_8$, OCOR$_8$, or $R_3$ denotes phenyl, which is optionally substituted by —OH, halogen, —OR$_8$, $C_1$–$C_4$-alkyl, preferably —CH$_3$—, —NH$_2$, —COOH, —SO$_3$H, —COOR$_8$, —OCH$_2$COOR$_8$, —CN, or —OCH$_2$CONR$_6$R$_7$, or $R_3$ denotes a norbornane-, norbornene-, a $C_3$–$C_6$-dicycloalkylmethyl, preferably dicyclopropylmethyl, adamantane- or noradamantane- group;

$R_3$ denotes —CH=CH-phenyl, wherein the phenyl ring is mono- or polysubstituted by methoxy, hydroxy or halogen;

$R_3$ denotes a [3.3.0]-bicyclooctane, preferably a [3.3.0]-bicyclooctan-2-yl;

$R_3$ denotes a C-linked piperidine or furan;

$R_4$ denotes hydrogen, methyl or benzyl, in which the benzyl group may be substituted by 1–3 methoxy groups; $CH_3$—O—$CH_2$— $CH_3$—S—$CH_2$—,

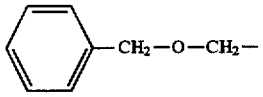

privaloyloxymethyl or —$CH_2$—CH=$CH_2$;

$R_5$ denotes $C_1$–$C_4$-alkyl, optionally substituted by OH, OCOR$_8$, NH$_2$, NR$_6$R$_7$ or NHCOR$_8$, and $R_5$ preferably represents —$CH_2$—$CH_2$—OH, —$CH_2CH_2OCOR_8$, —$CH_2$—$CH_2$—$CH_2$—OH; —$CH_2$—$CH_2CH_2OCOR_8$;

$R_6$ denotes hydrogen, an optionally substituted $C_{3-6}$-cycloalkyl group, a branched or unbranched alkyl-, alkenyl- or alkynyl group having up to 10 carbon atoms, preferably a $C_1$–$C_4$-alkyl group, which may optionally be substituted by hydroxy, phenyl, substituted phenyl, amino, substituted amino, $C_1$ to $C_8$, preferably $C_1$ to $C_4$-alkoxy, or it denotes —$(CH_2)_m$—$NHCO_8$ wherein m=1, 2, 3 or 4;

$R_7$ denotes hydrogen, an optionally substituted $C_{3-6}$-cycloalkyl group, a branched or unbranched alkyl-, alkenyl- or alkynyl group having up to 10, preferably 1–4, carbon atoms, which may optionally be substituted by hydroxy, phenyl, substituted phenyl, amino, substituted amino, $C_1$ to $C_8$, preferably $C_1$ to $C_4$-alkoxy, or it denotes —$(CH_2)_m$—NHCOOR$_8$ wherein m=1, 2, 3 or 4; preferably hydrogen, or $R_6$ and $R_7$ together with the nitrogen atom form a saturated or unsaturated 5- or 6-membered ring which may contain as heteroatoms nitrogen, oxygen or sulphur, whilst the heterocyclic ring may be substituted by a branched or unbranched $C_{1-4}$-alkyl group, preferably methyl, or may carry one of the following groups: —$(CH_2)_n$—NH$_2$, =O, a ketal—preferably —O—$CH_2$—$CH_2$—O—, —$(CH_2)_n$NH—$C_1$–$C_4$-alkyl, —$(CH_2)_n$—N $(C_1$–$C_8$-alkyl)$_2$, —$(CH_2)_n$—NHCOOR$_8$, (n=2, 3, 4,), halogen, —OR$_8$, —CN, —NO$_2$, —NH$_2$, —$CH_2NR_6R_7$, —OH, —COOH, —SO$_3$H, —COOR, —CONR$_6$R$_7$, —SO$_2$—R$_8$.

$R_8$ denotes hydrogen, $C_1$–$C_4$-alkyl, $C_2$–$C_4$-alkenyl, $C_2$–$C_4$-alkynyl, a benzyl- or phenyl- group, which is optionally mono- or polysubstituted by OCH$_3$;

$R_9$ denotes $C_1$–$C_4$-alkyl, $C_2$–$C_4$-alkenyl, $C_2$–$C_4$-alkynyl, optionally substituted phenyl, optionally substituted benzyl, $C_3$–$C_6$-cycloalkyl.

$R_{10}$ denotes —COOR$_8$, —$CH_2OR_8$, —CONR$_6$R$_7$, hydrogen, $C_1$–$C_3$-alkyl, optionally substituted phenyl, —$CH_2NR_6R_7$;

$R_{11}$ denotes hydrogen, phenyl, substituted phenyl, —$CH_3$; optionally in the form of the racemates, the enantiomers, the diastereomers and the mixtures thereof and optionally in the form of the pharmacologically acceptable salts thereof.

The compounds which are preferred as pharmaceutical compositions are the compounds of general formula I wherein $R_1$ does not denote hydrogen but $R_4$ is hydrogen, since compounds of general formula I wherein $R_1$=hydrogen have a lowering $A_1$-receptor-affinity; however, these compounds are of particular importance as intermediates.

Preferred compounds of general formula I are those wherein

R1=methyl, ethyl, n-butyl, allyl and preferably n-propyl;

$R_2$ denotes a $C_2$-alkyl or an unbranched $C_3$-alkyl group which is substituted by —CN, —$CH_2NR_6R_7$, —OH, —OR$_8$, —NR$_6$R$_7$, —NHCOR$_8$, —NHCONR$_6$H, halogen, —OCOR$_8$, —OCH$_2$COOH, —OCH$_2$COOR$_8$, —SR$_5$, —SO$_2$R$_5$, —OCH$_2$—CONR$_6$R$_7$, —OCH$_2$CH$_2$OH, OCH$_2$—CH$_2$—NR$_6$R$_7$, CONHSO$_2$R$_8$, —CH$_2$CONHSO$_2$R$_8$, —OCH$_2$CH$_2$OR$_8$, —COOH, —COOR$_8$, —CONR$_6$R$_7$, —CHO, —SR$_8$, —SO$_2$R$_8$, —SO$_3$H, —SO$_2$NR$_6$R$_7$, —OCH$_2$—CH$_2$OCOR$_8$, =NOH, =NOR$_8$, —COR$_9$, —CH(OH)R$_9$, —CH=CH—R$_{10}$, OCONR$_6$H

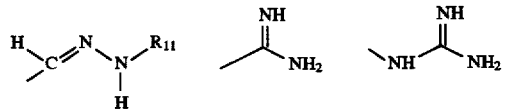

or by 1,3-dioxolane or 1,3-dioxane optionally mono- or polysubstituted, preferably monosubstituted, by methyl;

$R_2$ denotes a benzyl- or phenethyl- or phenylpropyl group which is substituted by one of the following groups —$C_1$–$C_3$-alkyl, —CN, —$CH_2NR_6R_7$, —NO$_2$, —OH, —OR$_8$, —NHCOR$_8$, —NHCONR$_6$R$_7$, halogen, —OCOR$_8$, —OCH$_2$COOH, —OCH$_2$COOR$_8$, —$CH_2OCOR_8$, —SO$_2$R$_5$, —OCH$_2$—CONR$_6$R$_7$, —OCH$_2$CH$_2$OH, —$CH_2$CONHSO$_2$R$_8$, —OCH$_2$—CH$_2$—NR$_6$R$_7$, —CONHSO$_2$R$_8$, —OCH$_2$CH$_2$OR$_8$, —COOH, —COOR$_8$, —CF$_3$, cyclopropyl, —CONR$_6$R$_7$, —$CH_2OH$, —$CH_2OR_8$, —CHO, —SR$_8$, —SOR$_8$, —SO$_2$R$_8$, —SO$_3$H, —SO$_2$NR$_6$R$_7$, —OCH$_2$—CH$_2$OCOR$_8$, —CH=NOH, CH=NOR$_8$, —COR$_9$, —CH(OH)R$_9$, —CH(OR$_8$)$_2$, —NHCOOR$_8$, —CH=CH—R$_{10}$, —OCONR$_6$R$_7$, —$CH_2$—O—CONR$_6$R$_7$, —$CH_2$—$CH_2$—O—CONR$_6$R$_7$,

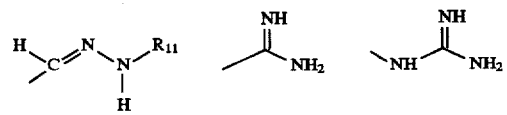

or by 1,3-dioxolane or 1,3-dioxane optionally mono- or polysubstituted, preferably monosubstituted, methyl, and if $R_2$ represents OR$_8$, particularly OCH$_3$, the phenyl group may be trisubstituted;

$R_2$ denotes a $C_3$-, $C_4$-, $C_5$- or $C_6$-cycloalkyl-$C_2$-$C_3$-alkylene group, wherein the cycloalkyl group is optionally monosubstituted by —CN, —$CH_2NR_6R_7$, =O, —OH, —OR$_8$, —NR$_6$R$_7$, —NHCOR$_8$, —NHCONR$_6$R$_7$, halogen, —OCOR$_8$, —OCH$_2$COOH, —OCH$_2$COOR$_8$, —$CH_2OCOR_8$, —SO$_2$R$_5$, —OCH$_2$—CONR$_6$R$_7$, —OCH$_2$CH$_2$OH, —OCH$_2$—CH$_2$—NR$_6$R$_7$, —OCH$_2$CH$_2$OR$_8$, —COOH, —COOR$_8$, —CONR$_6$R$_7$, —$CH_2OH$, —$CH_2OR_8$, —CHO, —SR$_8$, —SOR$_8$, —SO$_2$R$_8$, —SO$_3$H, —SO$_2$NR$_6$R$_7$, —OCH$_2$—CH$_2$OCOR$_8$, —CH=NOH, —CH=NOR$_6$, —COR$_9$, —CH(OH)R$_9$, —CH(OR$_8$)$_2$, —NHCOOR$_8$, —CONHSO$_2$R$_8$ —CH=CH—R$_{10}$, —OCONR$_6$R$_7$, —$CH_2$—O—CONR$_6$R$_7$, —$CH_2$—$CH_2$—O—CONR$_6$R$_7$,

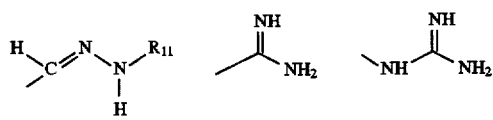

or by 1,3-dioxolane or 1,3-dioxane optionally mono- or polysubstituted, preferably monosubstituted by methyl;

$R_2$ denotes a group of the formula
A—CH$_2$—, A—CH$_2$—CH$_2$— A—CH$_2$—CH$_2$—CH$_2$—, A—CO—NH—CH$_2$—, A—CO—NH—CH$_2$—CH$_2$—, or A—CO—NH—CH$_2$—CH$_2$—CH$_2$—, wherein A is a C- or N-linked 5- or 6-membered heterocyclic ring which contains nitrogen, oxygen or sulphur as heteroatoms and which may optionally be mono- or polysubstituted by $C_{1-4}$-alkyl, =O, OH, COR$_9$, SO$_2$-R$_8$, COOR$_8$, CONR$_6$R$_7$, or OR$_8$;

and $R_3$, $R_4$, $R_5$, $R_6$, $R_7$, $R_8$, $R_9$, $R_{10}$ and $R_{11}$ are as hereinbefore defined, optionally in the form of the racemates, the enantiomers, the diastereomers and the mixtures thereof and optionally the pharmacologically acceptable salts thereof.

Particularly preferred % groups are cyclopentyl, wherein the cyclopentyl group may be substituted by =O, or mono- or disubstituted by —OH, —OR$_8$, particularly —OCH$_3$, or —OCOR$_8$, particularly OCOCH$_3$, and these groups are particularly preferred in conjunction with $R_1$=n-propyl and $R_4$=hydrogen of general formula Ia

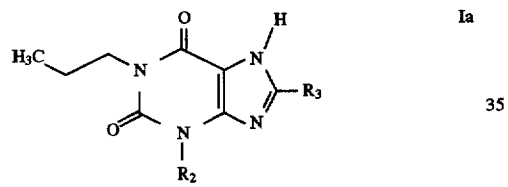

wherein $R_2$ is defined as hereinbefore.

Compounds of general formula I or Ia wherein $R_2$=an unbranched $C_{2-5}$-alkyl group substituted by —CN, —OH, SO$_2$—R$_5$, —O—C$_1$—C$_4$-alkyl, —COOH, —COOR$_8$, particularly COOCH$_3$ or —COOC$_2$H$_5$, —OCOCH$_3$, —OCOC$_2$H$_5$, —CONR$_6$R$_7$, =NOH, —NR$_6$R$_7$ or a C-linked 5- or 6-membered heterocyclic group containing nitrogen, are preferred inter alia.

Particularly preferred groups $R_2$ of general formulae I and Ia are:

—CH$_2$CH$_2$CH$_2$CN
—CH$_2$CH$_2$CH$_2$CH$_2$CH$_2$CN
—CH$_2$CH$_2$OCH$_3$
—CH$_2$CH$_2$CH$_2$OCH$_3$
—CH$_2$CH$_2$OH
—CH$_2$CH$_2$CH$_2$OH
—CH$_2$CH$_2$OCOCH$_3$
—CH$_2$CH$_2$CH$_2$OCOCH$_3$
—CH$_2$CH$_2$COOH
—CH$_2$CH$_2$COOCH$_3$
—CH$_2$CH$_2$CONH$_2$
—CH$_2$CH$_2$CONHCH$_3$

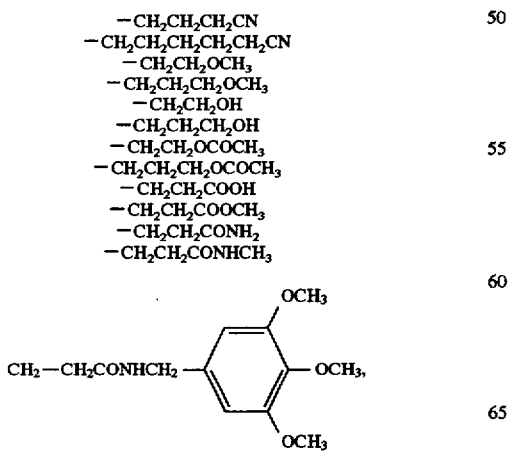

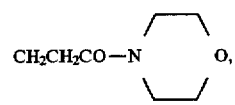

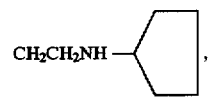

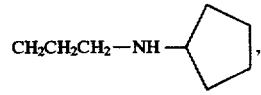

—CH$_2$CH$_2$NHCOCH$_3$
—CH$_2$CH(OH)CH$_2$OH
—CH$_2$CH$_2$CH(OH)CH$_3$
—CH$_2$CH=NOH
—CH$_2$CH$_2$CH$_2$CH$_2$NH$_2$

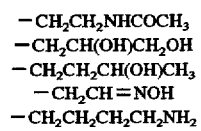

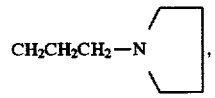

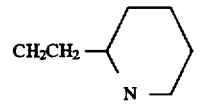

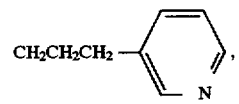

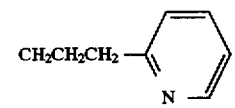

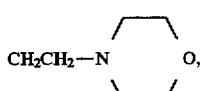

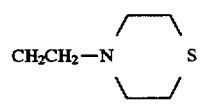

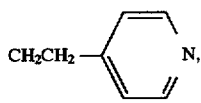

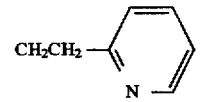

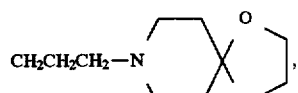

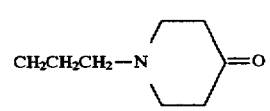

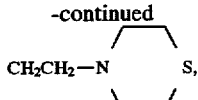
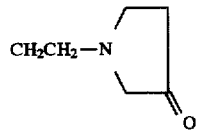
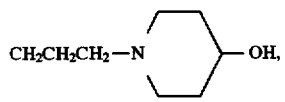
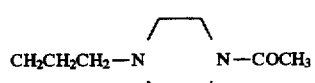
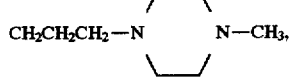
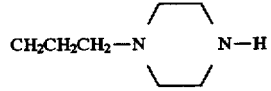
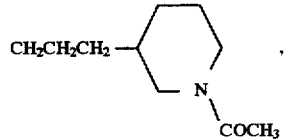
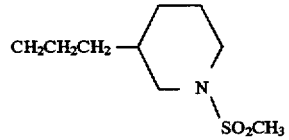
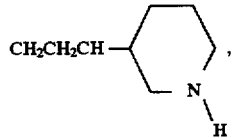
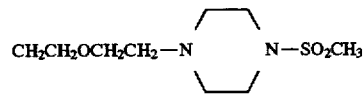
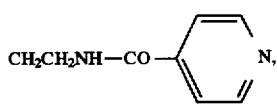
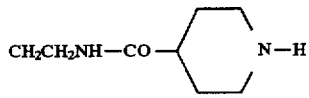

optionally in the form of the racemates, the enantiomers, the diastereomers and the mixtures thereof and optionally the pharmacologically harmless salts thereof.

Compounds of general formula I or Ia which are particularly readily water-soluble are those wherein $R_2$ denotes $-CH_2-CH_2COOH$, $-CH_2CH_2OH$, $-CH_2-CH_2-CH_2-OH$,

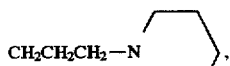
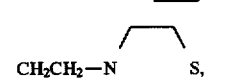
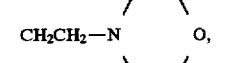
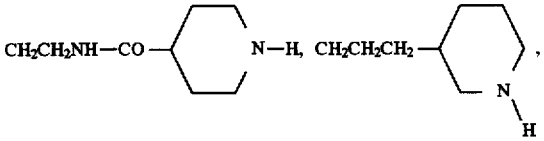

$CH_2CH_2SO_2CH_2CH_2OH$, $CH_2CH(OH)CH_2OH$,

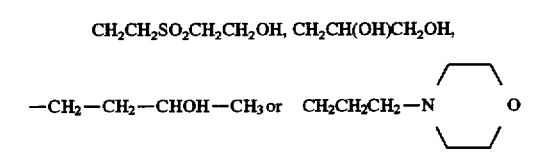

Although less readily water-soluble, compounds of general formula Ia wherein $R_2$ has the following groups are preferred on account of their pharmacological properties:

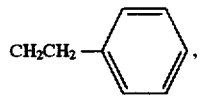 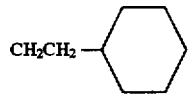
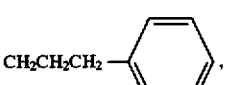 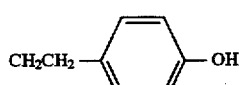
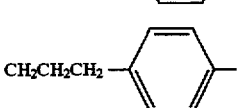 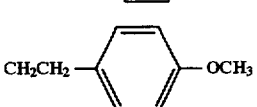
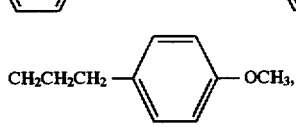
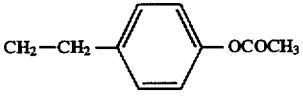
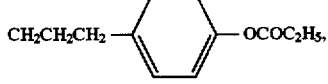
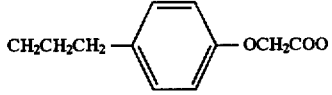

-continued

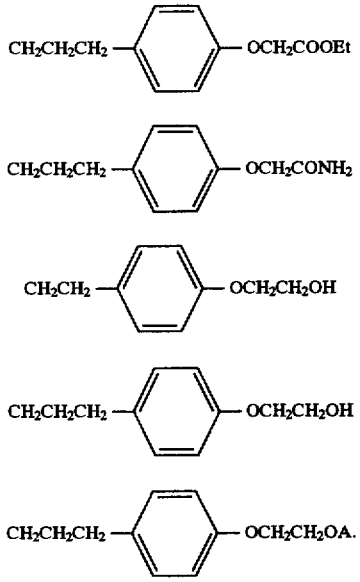

The following groups are particularly preferred:

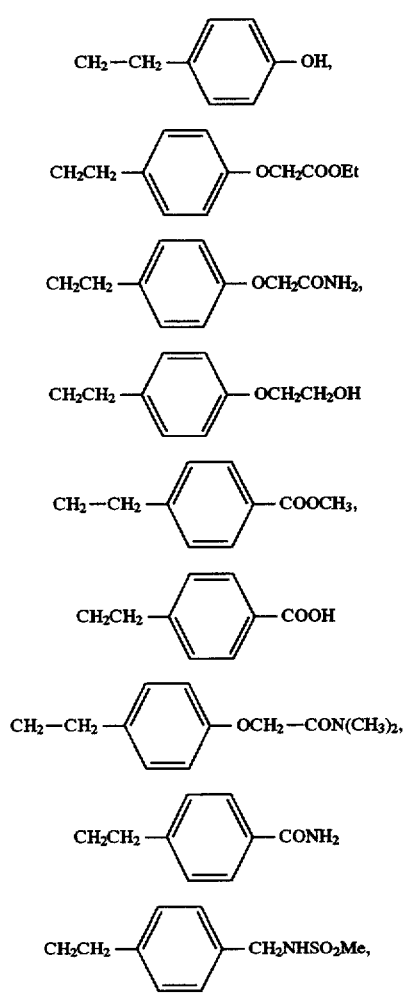

-continued

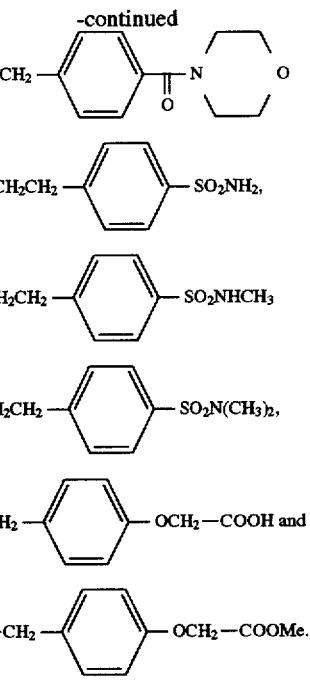

Also preferred are compounds of general formula Ia

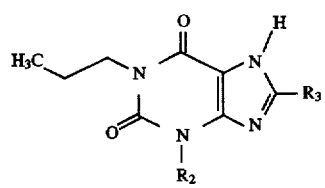

wherein
$R_3$ denotes a radical from the group

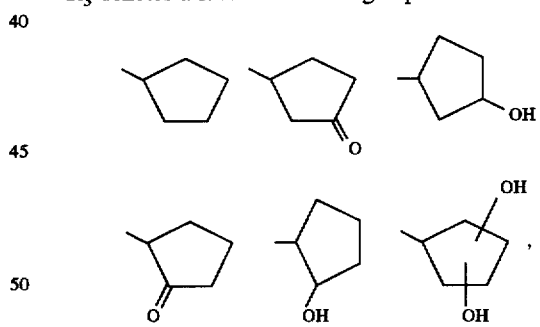

cyclopentyl being preferred, and $R_2$ denotes $CH_2CH_2OH$, $CH_2CH_2OCOCH_3$, $(CH_2)_3OCOCH_3$, $(CH_2)_3OCH_3$, $CH_2CH_2COCH_3$, $CH_2CH_2CH(OH)CH_3$, $CH_2CH_2COOCH_3$, $CH_2CH_2CONH_2$, $(CH_2)_3CONH_2$, $CH_2CH=NOH$, $(CH_2)_3CN$, $CH_2CH_2SCH_2CH_3$, $CH_2CH_2SCH_2CH_2OH$, $CH_2CH_2SO_2CH_2CH_2OH$, $CH_2CH_2SO_2CH_2CH_2OCOCH_3$, $R_2$ denotes A—$(CH_2)_2$— or A—$(CH_2)_3$—
wherein A is a C- or N-linked 5- or 6-membered heterocyclic ring containing nitrogen, oxygen or sulphur as heteroatoms, especially pyridine, morpholine, thiomorpholine, piperidine, tetrazol, the following groups R₂ being particularly preferred:

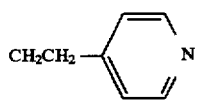

CH₂CH₂SCH₂CH₂OH,

CH₂CH₂SO₂CH₂CH₂OH,

CH₂CH₂OH,

CH₂CH₂CH₂OCH₃,

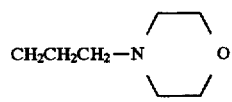

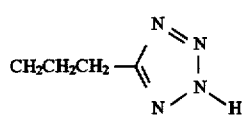

CH₂CH₂CH₂CONH₂,

CH₂CH=NOH,

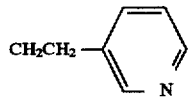

The following xanthine derivatives are of particular interest:

1-propyl-3-(2-(pyridin-4-yl)ethyl)-8-cyclopentyl-7H-purine-2,6-dione 1-propyl-3-(2-(2-hydroxyethyl)-thioethyl)-8-cyclopentyl-7H-purine-2,6-dione 1-propyl-3-(2-(2-hydroxyethyl)-sulfonylethyl)-8-cyclopentyl-7H-purine-2,6-dione 1-propyl-3-(2-hydroxyethyl)-8-cyclopentyl-7H-purine-2,6-dione 1-propyl-3-(3-methoxypropyl)-8-cyclopentyl-7H-purine-2,6-dione 1-propyl-3-(3-morpholin-1-yl-propyl)-8-cyclopentyl-7H-purine-2,6-dione 1-propyl-3-(3-tetrazol-5-yl-propyl)-8-cyclopentyl-7H-purine-2,6-dione 1-propyl-3-(3-(aminocarbonyl)propyl)-8-cyclopentyl-7H-purine-2,6-dione 1-propyl-3-(hydroxyiminoethyl)-8-cyclopentyl-7H-purine-2,6-dione 1-propyl-3-(3-pyridin-3-yl-propyl)-8-cyclopentyl-7H-purine-2,6-dione The term "alkyl groups" (even when they are components of other groups) refers to branched and unbranched $C_{1-10}$, preferably $C_{1-4}$-alkyl groups, for example: methyl, ethyl, n-propyl, iso-propyl, butyl, iso-butyl, sec.butyl, tert.-butyl, pentyl, iso-pentyl, hexyl, heptyl and octyl.

The term "alkenyl groups" denotes branched and unbranched $C_{2-10}$, preferably $C_{2-3}$-alkenyl groups, provided that they have at least one double bond, e.g. including the alkyl groups mentioned above provided that they have at least one double bond, such as vinyl (provided that no unstable enamines or enolethers are formed), propenyl, isopropenyl, butenyl, pentenyl and hexenyl.

Examples of alkynyl groups are $C_{2-10}$-alkynyl groups provided that they have at least one triple bond, such as ethynyl, propargyl, butynyl, pentynyl and hexynyl.

The term $C_{3-6}$-cycloalkyl groups denotes, for example, cyclopropyl, cyclobutyl, cyclopentyl or cyclohexyl, which may also be substituted by branched or unbranched $C_{1-4}$-alkyl, hydroxy and/or halogen or which may be substituted as hereinbefore defined. The word halogen generally refers to fluorine, chlorine, bromine or iodine.

Examples of cyclic groups of general formula NR₆R₇ include: pyrrole, pyrroline, pyrrolidine, 2-methylpyrrolidine, 3-methylpyrrolidine, piperidine, piperazine, N-methylpiperazine, N-ethylpiperazine, N-(n-propyl)-piperazine, N-benzylpiperazine, morpholine, thiomorpholine, imidazole, imidazoline, imidazolidine, pyrazole, pyrazoline, pyrazolidine—the above-mentioned heterocycles may be substituted by $C_{1-4}$-alkyl, preferably methyl, or carry one of the following groups:

—(CH₂)ₙ—NH₂, a ketal,

—(CH₂)ₙNH—C₁-C₄-alkyl,

—(CH₂)ₙ—N(C₁-C₈-alkyl)₂, =O,

—(CH₂)ₙ—NHCOOR, (n=2, 3, 4), halogen,

—OR₈, —CN, —NO₂, —NH₂, —CH₂NR₆R₇,

—OH, —COOH, —SO₃H, —COOR₈, —CONR₆R₇,

—CONR₆R₇.

Examples of C-linked 5- or 6-membered heterocyclic rings which may contain nitrogen, oxygen or sulphur as heteroatoms, include tetrahydrofuran, 2-methyltetrahydrofuran, 2-hydroxymethylfuran, tetrahydrofuranone, γ-butylrolactone, α-pyran, γ-pyran, tetrahydropyran, pyrrole, pyrroline, pyrrolidine, piperazine, morpholine, thiomorpholine, imidazole, imidazoline, imidazolidine, pyrazole, pyrazoline, triazole, tetrazole, oxazole, oxadizole, pyrazolidine, whilst the heterocycle may be substituted as specified in the definitions.

"=O" denotes an oxygen atom linked via a double bond.

Xanthine derivatives with a high adenosine-A₁-affinity promote neurotransmission in the brain and can be regarded for example as functional cholinomimetics.

Substances of this kind are of great interest for the symptomatic treatment of degenerative disorders of the central nervous system such as senile dementia and Alzheimer's disease.

The high receptor affinity should make it possible to treat patients with low doses, so that virtually no side effects can be expected which cannot be traced back to the blockade of adenosine receptors. In addition to their use as gerontopsychopharmaceuticals and nootropics, the adenosine antagonists described could be useful in the treatment of cardiac and circulatory disorders and in the treatment of respiratory disorders, particularly bronchial asthma. Furthermore, xanthines of, general formula I exhibit diuretic properties and are thus of interest in the treatment of kidney disease and, because of their diuretic properties, for treating high blood pressure.

Other possible indications are degenerative illnesses such as organic brain syndrome, Parkinson's disease, depression, traumatic CNS-damage, post stroke neurological deficit, respiratory depression (intoxication, post op) neonatal brain trauma, dyslexia and hyperactivity. Compounds of general formula I, wherein R₃ has an optionally substituted phenylvinylene group are proposed for the treatment of Parkinson's disease.

Cystic fibrosis—also known as mucoviscidosis—is a hereditary disorder caused by a genetic defect on a certain chromosome. Only homozygotic carriers of the feature succumb to the disease. The genetic defects leads to the .dysfunction of exocrine glands. As a result of increased production and greater viscosity of the secretions of the mucous glands in the bronchi, severe complications may arise in the respiratory tract. Preliminary investigations have shown that $A_1$-antagonists increase the efflux of chloride ions, e.g.,in CF PAC cells. The cells come from a pancreas adenocarcinoma cell line which was isolated from patients suffering from cystic fibrosis (CF). The activity was successfully blocked by agonists such as 2-chloroadenosine. Interestingly, an increase in the efflux was observed only in those cells which came from patients suffering the disease or having the corresponding genetic defect.

Starting from these findings it is to be expected that, in patients suffering from cystic fibrosis (mucoviscidosis), the compounds according to the invention will regulate the disrupted electrolyte management of the cells and will alleviate the symptoms of the disease.

Adenosine antagonists can be used to treat lung diseases, particularly asthma, allergic lung diseases and chronically obstructive lung diseases. It is to be expected that the compounds according to the invention will also be suitable for the treatment of lung diseases by inhalation, because of their high potency.

The receptor binding values were determined analogously to Ensinger et al. in "Cloning and functional characterisation of human $A_1$ adenosine receptor—Biochemical and Biophysical Communications, Vol 187, No. 2, 919–926, 1992".
Effect on the inhibition of locomotor activity in the mouse achieved by adenosine antagonists: adenosine-antagonism:

Subcutaneous administration of an adenosine-agonist was able to induce inhibition of locomotor activity in mice in the hour following administration. The test is to determine how a test substance will influence this hypomotility.

The measurements for this test are concerned with the number of times a light beam is broken in motility chambers. The figures are recorded by computer immediately after the substance has been administered. Only the first hour after administration is evaluated, since the activity of adenosine agonist occurs during this period.

In addition to the mice which are given both the adenosine agonist and the test substance, one group is given placebo (tylose and NaCl solution), one is given the adenosine agonist and tylose solution and one group is given the maximum dose of the test substance and NaCl solution. The individual animals of all the treatment groups are tested in separate measuring chambers over the same period of time.

TABLE Ia

| Examples according to Table I | Ki[nMol/l] $A_1$ | Locom. (mg/kg) |
|---|---|---|
| 01 | 7.5 | 3.0 |
| 04 | 8.0 | 0.6 |
| 05 | 46.7 | 0.6 |
| 06 | 66.8 | 0.6 |
| 07 | 2.7 | |
| 08 | 3.5 | 10.0 |
| 10 | 3.1 | 10.0 |
| 11 | 4.0 | 0.6 |
| 14 | 36.4 | 2.5 |
| 15 | 6.4 | 0.6 |
| 17 | 3.8 | 0.6 |
| 19 | 11.5 | 0.6 |
| 24 | 1.7 | |
| 28 | 29.3 | |
| 31 | 9.1 | 10.0 |
| 47 | 2.1 | 2.5 |
| 52 | 5.0 | 0.6 |
| 59 | 2.0 | 0.6 |
| 60 | 3.8 | 0.6 |
| 68 | 32.6 | 2.5 |
| 70 | 6.2 | 0.6 |

The compounds according to the invention can be prepared by analogous methods known per se as illustrated, for example, in synthesis plans I, II and III. The person skilled in the art is familiar enough with the synthesis of xanthines, but the following experimental section will explain it in detail once more with reference to some important key compounds.

Synthesis plan I

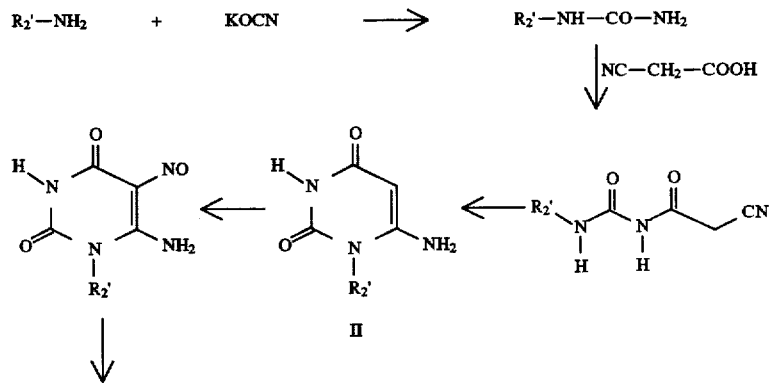

Synthesis plan I -continued

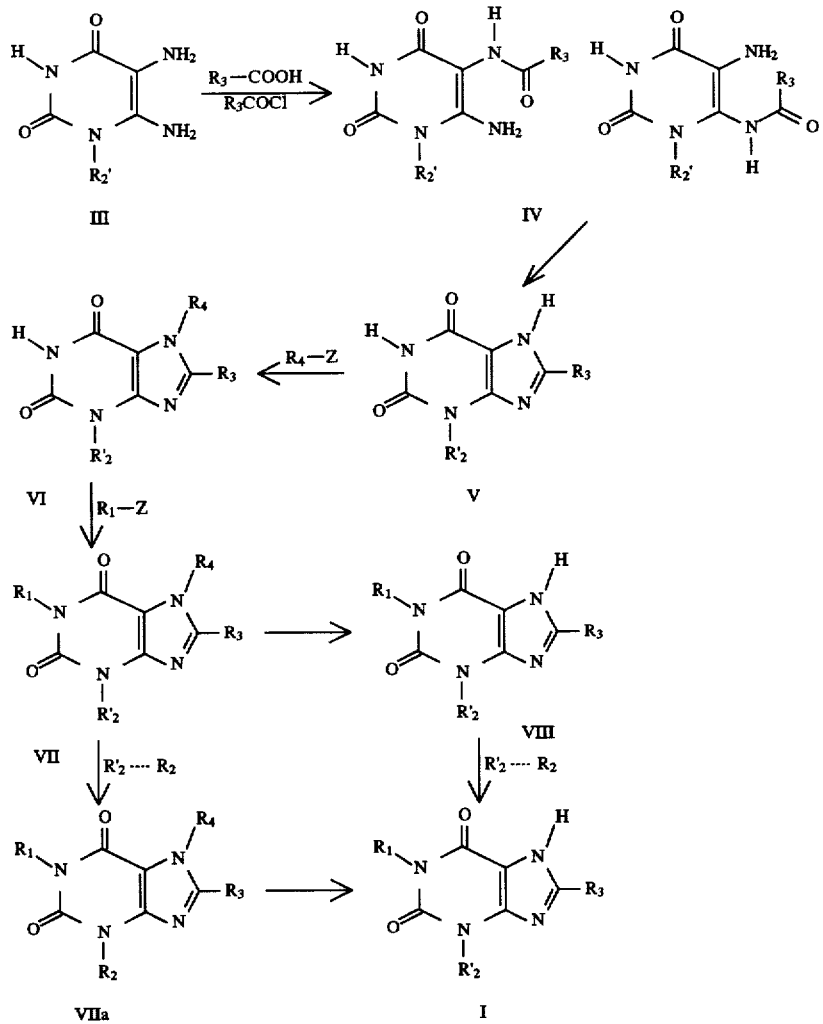

A characteristic feature of the synthesis illustrated in plan I is that $R_2'$ is introduced at the diaminouracil stage (III). $R_2'$ is a functional group, selected from the group of definitions of $R_2$ with the proviso that $R_2'$ must not interfere with the synthesis of the xanthine and can be converted into the desired $R_2$ of general formula I before or after the cleavage of the protecting group $R_4$ (preferably benzyl) (formula VIII). A preferred definition of $R_2'$ is a methoxybenzyl group, for example. $R_3$ is inserted by aminoacylation and subsequent cyclisation to form the xanthine. In order to be able to carry out alkylation deliberately in 1-position, it is necessary to protect the 7-position, e.g. using a benzyl group. The alkylations are carried out by reacting with $R_4$-Z, wherein $R_4$=benzyl or methyl and Z is a readily cleavable group such as halogen, mesyl or tosyl. In case $R_4$ denotes a methyl group in the final compound of general formula I, the xanthine V is already irreversibly methylated at this stage.

$R_1$ is then inserted into the protected xanthine VI by N-alkylation. The conversion of $R_4$ into hydrogen can then be carried out by cleaving the protecting group in the 7-position. If $R_2'$ has not yet assumed the desired definition $R_2$ of the end compound I, $R_2'$ can now be converted into $R_2$ (formula VIIa) and, if this has not yet happened, the protecting group is then split off. Examples of this are described in the general operation instructions under points 12 and 14 to 23. The compounds of general formula II and III are important intermediates and are claimed as such. It has been found, surprisingly, that a p-methoxybenzyl group or a di- or trimethoxybenzyl group in the 3-position of the xanthine of formula IX can be selectively cleaved in order to obtain the benzyl protecting group in the 7-position. This opens up a new method of obtaining xanthine derivatives of general formula I. By alkylating xanthines of general formula X with $R_2'$—X (X=halogen, OH, mesyl or tosyl), cleaving the benzyl protecting group and optionally converting $R_2'$ into $R_2$, compounds of general formula I can be obtained in a simple manner.

The invention also relates to a simple and generally applicable method of preparation for synthesising xanthine derivatives substituted in the 1- and 3-positions, wherein $R_1$ and $R_2$ may represent any desired groups, provided that they can be inserted by an electrophilic reaction.

Synthesis plan II
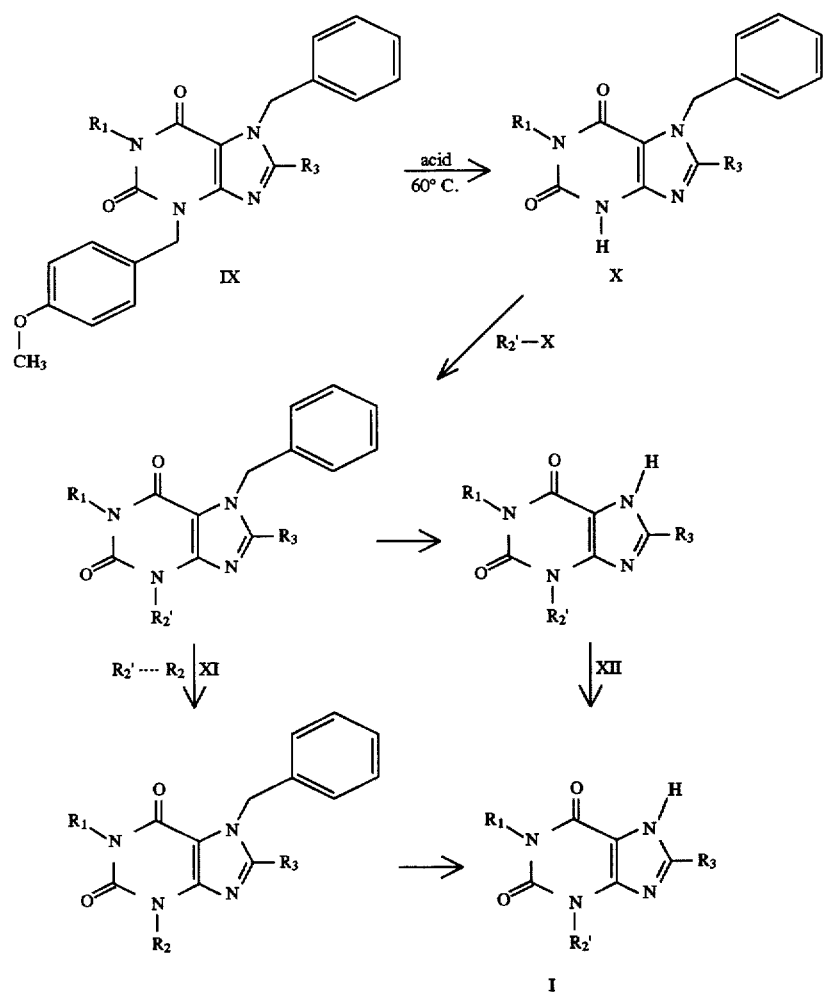
Compounds of general formula X (R$_4$-benzyl) can easily be obtained by acid hydrolysis (e.g. with formula IX wherein R$_4$=benzyl and R$_2$=p-methoxybenzyl).
Synthesis plan III
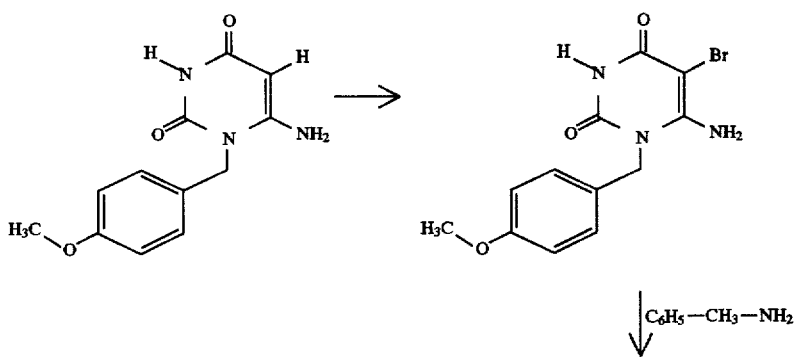

-continued
Synthesis plan III

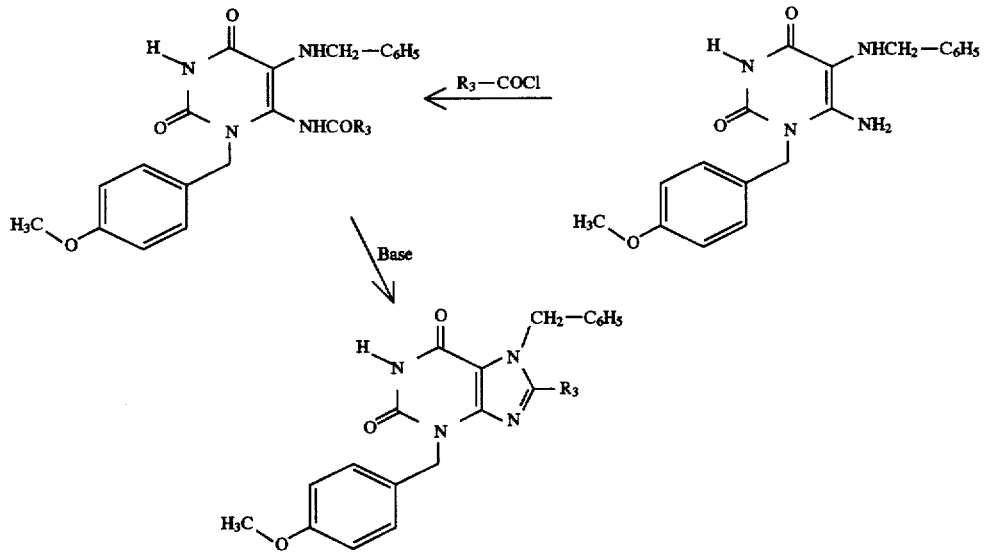

The following are general operative instructions in order to prepare the compounds according to the invention.

1. Monosubstituted ureas:

0.69 mol of amine are dissolved in a solution of 18.3 ml (0.34 mol) of conc. $H_2SO_4$ and 1000 ml of distilled water. The mixture is heated to 85° C., 55.8 g (0.69 mol) of KOCN are added and the resulting mixture is stirred at this temperature until the reaction is complete (30–90 min.). The reaction mixture is diluted with ethanol, cooled to ambient temperature and filtered. The filtrate is evaporated down and the solid residue is dried in a drying cupboard.

The following monosubstituted ureas, inter alia, were prepared in this way:
a) p-methoxybenzylurea, 85.5 % of theory, mp.=156°–158° C.
b) 2-(p-methoxyphenyl)-ethylurea, 91.4% of theory, mp.=127° C.
c) 3-(p-methoxyphenyl)-propylurea, 91.8% of theory, mp.=170°–173° C.
d) 2-methoxyethylurea, 97.3% of theory, mp.=72° C.
e) 3-methoxypropylurea, 92.2% of theory, mp.=79°–81° C.
f) 2-(p-chlorophenyl)-ethylurea, 73.2% of theory, mp.=150°–151° C.
g) 2-(p-bromophenyl)-ethylurea, 92.3% of theory, mp.=18320 –184° C.
h) 3-(p-chlorophenyl)-propylurea, 82.4% of theory, mp.=14620 –150° C.

2. Substituted cyanoacetylureas:

220 ml of acetanhydride are mixed with 57.6 g (0.68 mol) of cyanoacetic acid and 0.62 Mol of monosubstituted urea [see 1.]. The mixture is heated to 75°–80° C. and stirred at this temperature until the reaction is complete (30–90 min.). It is then cooled, diluted with ether and suction filtered and the crystalline product is washed with ether. The following cyanoacetylureas, inter alia, were prepared in this way:
a) N-(p-methoxybenzyl)-N'-cyanoacetylurea, 81.3% of theory, mp.=185° C.
b) N-(2-(p-methoxyphenyl)-ethyl)-N'-cyanoacetylurea, 69% of theory, mp.=142°–151° C.
c) N-(3-(p-methoxyphenyl)-propyl)-N'-cyanoacethylurea, 83.7% of theory, mp.=162°–164° C.
d) N-2-methoxyethyl-N'-cyanoacetylurea, 78.9% of theory, mp.=129°–132° C.
e) N-3-methoxypropyl-N'-cyanoacetylurea, 74.4% of theory, mp.=138°–140° C.
f) N-(2-(p-chlorophenyl)-ethyl)-N'-cyanoacetylurea, 59.5% of theory, mp.=192°–193° C.
g) N-(2-(p-bromophenyl)-ethyl)-N'-cyanoacetylurea, 80.2% of theory, mp.=192°–193° C.

3. 1-Substituted 6-aminouracils:

0.5 mol of substituted cyanoacetylurea [see 2.] is placed in 1250 ml of absolute ethanol and heated to 50°–80° C. A solution of 3.8 g (0.17 mol) of sodium in 190 ml of absolute ethanol is added dropwise and the resulting suspension is stirred for 30 minutes at reflux temperature. The mixture is diluted with distilled water, cooled, optionally neutralised with HCl and the crystalline product is suction filtered.

The following 1-substituted 6-aminouracils were prepared, inter alia, using this method:
a) 6-amino-1-(p-methoxybenzyl)-uracil, 63.3% of theory, mp.=276°–278° C.
b) 6-amino-1-(2-(p-methoxyphenyl)-ethyl)-uracil, 69% of theory, mp.=233°–236° C.
c) 6-amino-1-(3-(p-methoxyphenyl)-propyl)uracil, 69.3% of theory
d) 6-amino-1-(2-methoxyethyl)-uracil, 41.6% of theory, mp.=229°–230° C.
e) 6-amino-1-(3-methoxypropyl)-uracil, 68.1% of theory, mp.=208°–210° C.
f) 6-amino-1-(2-(p-chlorophenyl)-ethyl)-uracil, 78.1% of theory, mp.=282°–283° C.
g) 6-amino-1-(2-(p-bromophenyl)-ethyl)-uracil, 56.1% of theory, mp.=291°–292° C.

4. 1-Substituted 6-amino-5-nitrosouracils:

0.005 mol of 1-substituted 6-aminouracil [see 3.] is suspended in 12.5 ml of distilled water; in the case of starting compounds which are particularly difficult to dissolve, ethanol is also added. The mixture is heated to 80° C. and combined with a solution of 0.36 g (5.3 mMol) of sodium nitrite in 3 ml of distilled water. Then 0.7 ml of glacial acetic acid are added and the mixture is stirred at 80° C. until the reaction has ended. The reaction mixture is cooled, the reddish-violet residue is suction filtered and washed with distilled water.

The following 1-substituted 6-amino-5-nitrosouracils were prepared, inter alia, using this method:

a) 6-amino-5-nitroso-1-(p-methoxybenzyl)-uracil, 90.6% of theory, mp.=233° C.
b) 6-amino-5-nitroso-1-(2-(p-methoxyphenyl)-ethyl)-uracil, 75.8% of theory, mp.=227° C.
c) 6-amino-5-nitroso-1-(3-(p-methoxyphenyl)-propyl)-uracil, 49.1% of theory,
d) 6-amino-5-nitroso-1-(2-methoxyethyl)-uracil, 80% of theory, mp.=222° C.
e) 6-amino-5-nitroso-1-(3-methoxypropyl)-uracil, 58.5% of theory, mp.=227°–228° C.
f) 6-amino-5-nitroso-1-(2-(p-chlorophenyl)-ethyl)-uracil, 88.5% of theory, mp.=235°–236° C.
g) 6-amino-5-nitroso-1-(2-(p-bromophenyl)-ethyl)-uracil, 76.6% of theory, mp.=248° C.

5. 1-Substituted 5,6-diaminouracils 4.5 mMol of 1-substituted 6-amino-5-nitrosouracil [see 4.] are dissolved in 50 ml of conc. ammonia; for starting compounds which are particularly difficult to dissolve, ethanol is added. At 30° C. a solution of 2.35 g (13.5 mMol) of sodium dithionite in 24 ml of distilled water is added dropwise. The mixture is stirred at ambient temperature until the reaction has ended, then the crystalline product is suction filtered and washed with distilled water.

The following 1-substituted 5,6-diaminouracils, inter alia, were prepared using this method:
a) 5,6-diamino-1-(p-methoxybenzyl)-uracil, 93.2% of theory, mp.=252° C.
b) 5,6-diamino-1-(2-(p-methoxyphenyl)-ethyl)-uracil, 88.5% of theory, mp.=249°–250° C.
c) 5,6-diamino-1-(3-(p-methoxyphenyl)-propyl)-uracil, 80.5% of theory, mp.=252°–253° C.
d) 5,6-diamino-1-(2-methoxyethyl)-uracil, 84.4% of theory, mp.=246° C.
e) 5,6-diamino-1-(3-methoxypropyl)-uracil, 58.5% of theory, mp.=248° C. (decomposition)
f) 1-(2-(p-chlorophenyl)-ethyl)-5,6-diaminouracil, 66.3% of theory, mp.=279°–280° C.
g) 1-(2-(p-bromophenyl)-ethyl)-5,6-diaminouracil, 79.7% of theory, mp.=273° C. (decomposition)

6. 1-Substituted 6-amino-5-acylaminouracils and 1-substituted 5-amino-6-acylaminouracils The acylating position (5- or 6-position) is not important for the following reaction and has not been determined. In the interests of simplicity, the name of the product acylated in the 5-position is given hereinafter.

0.46 ml of 1-substituted 5,6-diaminouracil [see 5.] are suspended together with 78.2 g (0.64 mol) of 4-dimethylaminopyridine (DMAP) in 2400 ml of absolute dimethylformamide (DMF). At 0°–5° C. a solution consisting of 0.55 mol of the corresponding acid chloride in 200 ml of absolute DMF is added dropwise thereto, the mixture is stirred, whilst cooling with ice, until the reaction has ended and is then allowed to come up to ambient temperature. The reaction mixture is evaporated to dryness, the residue is triturated with distilled water. The crystalline product is suction filtered and washed with distilled water and diethylether.

The following title compounds were prepared, inter alia, using this method:
a) 6-amino-5-cyclopentylcarbonylamino-1-(p-methoxybenzyl)uracil, 88.3% of theory, mp.=261°–262° C.
b) 6-amino-5-cyclopentylcarbonylamino-1-(2-(p-methoxyphenyl)-ethyl)-uracil, 80.6% of theory, mp.= 217°–222° C.
c) 6-amino-5-cyclopentylcarbonylamino-1-(3-(p-methoxyphenyl)-propyl)-uracil, 84.8% of theory, mp.= 126°–128° C.
d) 6-amino-5-cyclopentylcarbonylamino-1-(2-methoxyethyl)uracil 84.4% of theory, mp.=209°–213° C.
e) 6-amino-5-cyclopentylcarbonylamino-1-(3-methoxypropyl)uracil, 84% of theory,
f) 6-amino-5-cyclopentylcarbonylamino-1-(2-(p-chlorophenyl)-ethyl)-uracil, 66.3% of theory, mp.= 258°–259° C.
g) 6-amino-5-cyclopentylcarbonylamino-1-(2-(p-bromophenyl)-ethyl)-uracil, 68.5% of theory, mp.= 245°–246° C.

7. Xanthines substituted in the 3- and 8-positions 0.01 mol of 1-substituted 6-amino-5-acylaminouracil (or 1-substituted 5-amino-6-acylaminouracil) [see 6.] are suspended in 10 ml of tetrahydrofuran and combined with a solution of 2.38 g (0.056 mol) of lithium hydroxide-hydrate in 70 ml of distilled water. The reaction mixture is stirred at 70°–80° C. until the reaction has ended, then made acidic with HCl and left to cool. The crystalline product is suction filtered and washed with distilled water. If necessary, it is recrystallised from ethanol in order to purify it.

The following xanthines substituted. in the 3- and 8-positions were prepared, inter alia, by this method:
a) 8-cyclopentyl-3-(p-methoxybenzyl)-xanthine, 77.8% of theory, mp.=311° C.
b) 8-cyclopentyl-3-(2-(p-methoxyphenyl)-ethyl)-xanthine, 42.3% of theory, mp.=256°–258° C.
c) 8-cyclopentyl-3-(3-(p-methoxyphenyl)-propyl)-xanthine, 90.5% of theory, mp.=292°–293° C.
d) 8-cyclopentyl-3-(2-methoxyethyl)-xanthine, 68.3% of theory, mp.=293°–294° C.
e) 8-cyclopentyl-3-(3-methoxypropyl)-xanthine, 90.9% of theory, mp.=240°–247° C.
f) 8-cyclopentyl-3-(2-(p-chlorophenyl)-ethyl)-xanthine, 81.3% of theory, mp.=298°–299° C.
g) 8-cyclopentyl-3-(2-(p-bromophenyl)-ethyl)-xanthine, 60.1% of theory, mp.=306°–307° C.

8. 7-Benzylxanthines substituted in 9- and 8-positions 0.02 Mol of xanthine substituted. in the 3- and 8-positions [see 7.] and 3.0 g (0.022 mol) of potassium carbonate are suspended in 140 ml of absolute DMF. The mixture is stirred for one hour at ambient temperature and then 2.62 ml (0.022 mol) of benzylbromide are added dropwise. The mixture continues to be stirred at ambient temperature. If the reaction stops before all the starting compounds have been reacted, up to 35 mol % of potassium carbonate and benzylbromide may be added. After the reaction has ended the mixture is evaporated to dryness, the residue is taken up in methylene chloride and extracted with water. The organic phase is dried with sodium sulphate and evaporated to dryness. The residue is purified by crystallisation or by chromatography.

Using this method, the following 7-benzylxanthines substituted in the 3- and 8-positions, inter alia, were prepared:
a) 7-benzyl-8-cyclopentyl-3-(p-methoxybenzyl)-xanthine, 66.2% of theory, mp.=165° C.
b) 7-benzyl-8-cyclopentyl-3-(2-(p-methoxyphenyl)-ethyl)-xanthine, 77% of theory, mp.=152° C.
c) 7-benzyl-8-cyclopentyl-3-(3-(p-methoxyphenyl)-propyl)-xanthine, 64% of theory, mp.=146°–148° C.
d) 7-benzyl-8-cyclopentyl-3-(2-methoxyethyl)-xanthine, 69.1% of theory, mp.=140° C.
e) 7-benzyl-8-cyclopentyl-3-(3-methoxypropyl)-xanthine, 77.7% of theory, mp.=130°–132° C.
f) 7-benzyl-8-cyclopentyl-3-(2-(p-chlorophenyl)-ethyl)-xanthine, 39.8% of theory, mp.=179°–180° C.

9. 7.Benzylxanthine substituted in the 1-, 3- and 8-positions 6.5 mMol of 7-benzylxanthine substituted in the 3- and 8-positions [see 8.], 1.0 g (7.15 mMol) of potassium carbonate and 7.15 mMol of alkyl-, alkenyl- or alkynylhalide are stirred in 56 ml of absolute DMF until the starting substance has reacted completely (if necessary, some more potassium carbonate and alkylhalide may be added). The reaction mixture is neutralised, evaporated down, the residue is taken up in methylene chloride and extracted with distilled water. The organic phase is dried with sodium sulphate and evaporated to dryness and the residue is purified, if necessary, by crystallisation or by chromatography.

Using this method, the following 7-benzylxanthines substituted in the 1-, 3- and 8-positions were prepared, inter alia:
a) 7-benzyl-8-cyclopentyl-3-(p-methoxybenzyl)-1-propylxanthine, 99% of theory, mp.=110°–111° C.
b) 7-benzyl-8-cyclopentyl-3-(2-(p-methoxyphenyl)-ethyl)-1-propylxanthine, 77% of theory, mp.=151° C.
c) 7-benzyl-8-cyclopentyl-3-(3-(p-methoxyphenyl)-propyl)-1-propylxanthine, 95.3% of theory, mp.=99°–101° C.
d) 7-benzyl-8-cyclopentyl-3-(2-methoxyethyl)-1-propylxanthine, 97.7% of theory, mp.=80°–81° C.
e) 7-benzyl-8-cyclopentyl-3-(3-methoxypropyl)-1-propylxanthine, 61.8% of theory, mp.=76°–80° C.
f) 7-benzyl-8-cyclopentyl-3-(2-(p-chlorophenyl)-ethyl)-1-propyl-xanthine, 67.9% of theory, colourless oil
g) 1-allyl-7-benzyl-8-cyclopentyl-3-(3-methoxypropyl)-xanthine, 86.5%, colourless oil Numerous other xanthine derivatives described by the general formula were prepared from the xanthines thus obtained by varying the substituents in the 3-position. Only those methods which are familiar to those skilled in the art were used.

10. 7-Benzylxanthines substituted in the 1- and 8-positions 6.3 mMol of 7-benzyl-3-p-methoxybenzylxanthine substituted in the 1- and 8-positions [see 9.] were mixed with 30 ml of trifluoroacetic acid and stirred for 4 days at 60° C. under a protective gas atmosphere. The mixture was diluted with distilled water, extracted with ethyl acetate, and the combined organic phases were dried with sodium sulphate and evaporated to dryness. The residue was purified by crystallisation or by chromatography.

Using this method, the following title compound was prepared, inter alia:
a) from 7-benzyl-8-cyclopentyl-3-(2-p-methoxybenzyl)-1-propylxanthine: 7-benzyl-8-cyclopentyl-1-propylxanthine, 90% of theory, mp.=214° C.

11. Introduction of substituents into the 3-position of 7-benzylxanthines substituted in the 2- and 8-positions Method A:

0.5 mMol of 7-benzylxanthine substituted in the 1- and 8-positions [see 10.], 75 mg (0.55mMol) of potassium carbonate and 0.55 mMol (optionally substituted, as described under $R_2$) of alkyl-, alkenyl- or alkynyl halide are stirred in 3.5 ml of absolute DMF until the reaction has ended, optionally with heating. The mixture is neutralised, evaporated to dryness and the residue is distributed between methylene chloride and distilled water. The organic phase is dried over sodium sulphate and evaporated down and the residue is purified, if necessary, by crystallisation or by chromatography.

Using this method, the following title compound was prepared, inter alia:
a) from 7-benzyl-8-cyclopentyl-1-propylxanthine: 7-benzyl-8-cyclopentyl-3-(Z-(p-methoxycarbonylphenyl)ethyl)-1-propylxanthine, 67% of theory, viscous oil Method B:

To a solution of 0.56 g (2.1 mMol) of triphenylphosphine in 3.5 ml of absolute tetrahydrofuran (THF) are added, successively, 0.37 g (2.1 mMol) of diethylazodicarboxylate (DEAD) and 1.4 mMol of 7-benzylxanthine substituted in the 1- and 8-positions [see 10] and the mixture is cooled to 5° C. At this temperature, 1.4 mMol of (optionally substituted, as described in $R_2$) alkyl-, alkenyl- or alkynylalcohol are added dropwise and the mixture is stirred at ambient temperature until all the starting substance has reacted. The mixture is evaporated to dryness and the residue is purified by crystallisation or by chromatography.

Using this method, the following title compounds were prepared, inter alia:
from 7-benzyl-8-cyclopentyl-1-propylxanthine:
a) 7-benzyl-8-cyclopentyl-1-propyl-3-(2-(2'pyridyl)-ethyl)-xanthine, 87% of theory, colourless oil
b) 7-benzyl-8-cyclopentyl-1-propyl-3-(3-(3-pyridyl)-propyl)-xanthine
c) 7-benzyl-3-(2-(p-cyanophenyl)-ethyl)-8-cyclopentyl-1-propyl-xanthine, 29.7% of theory, colourless oil Using the methods 11. A) and 11. B), many of the substituents $R_2$ described in the general formula were introduced directly or in the form of suitable precursors which were converted into the desired group $R_2$ by conventional methods.

12. Hydrolysis of methylethers

Method A:

0.5 mMol of methylether-derivative are dissolved in 5 ml of absolute acetonitrile. 300 mg (40 mMol) of sodium iodide are added followed by 0.39 ml (3.0 mMol) of chlorotrimethytsilane and the suspension is stirred at ambient temperature or at reflux temperature until the reaction has ended. The mixture is cooled to ambient temperature, mixed with distilled water and extracted with methylene chloride. The combined organic phases are washed with sodiumthiosulphate solution, dried over sodium sulphate and evaporated to dryness. The product is purified by crystallisation or chromatography, if required. Using this method the following title compounds were prepared, inter alia:
a) 7-benzyl-8-cyclopentyl-3-(3-hydroxypropyl)-1-propylxanthine, 78.4% of theory, yellowish oil
b) 7-benzyl-8-cyclopentyl-3-(2-hydroxyethyl)-1-propylxanthine, 90% of theory, mp.=208°–209° C.

Method B:

4.8 mMol of methylether-derivative are dissolved in 60 ml of absolute methylene chloride; At −20°±5° C. a solution of 0.65 ml (6.5 mMol) of boron tribromide in 7 ml of absolute methylene chloride is added dropwise and the resulting mixture is stirred at ambient temperature until the reaction has ended. The reaction mixture is washed with distilled water, the organic phase is dried over sodium sulphate and evaporated to dryness. The residue is purified by crystallisation or by chromatography.

Using this method, the following title compounds were prepared, inter alia:
a) 8-cyclopentyl-3-(2-hydroxyethyl)-1-propylxanthine, 80.7% of theory, mp.=216° C.
b) 8-cyclopentyl-3-(2-(p-hydroxyphenyl)-ethyl)-1-propylxanthine, 83.5% of theory, mp.=270°–272° C.
c) 7-benzyl-8-cyclopentyl-3-(3-(p-hydroxyphenyl)-propyl)-1-propylxanthine, 97.3% of theory, mp.=130°–132° C.
d) 7-benzyl-8-cyclopentyl-3-(3-hydroxypropyl)-1-propylxanthine, 83.6% of theory, mp.=116°–117° C.

13. Hydrogenolysis of N-benzyl substituents

Method A:

0.01 mol of N-benzyl compound are hydrogenated together with 0.5 g of palladium on activated charcoal or Pearlman catalyst in methanol, tetrahydrofuran or in glacial acetic acid under pressure and optionally with heating until all the starting compound has reacted. The catalyst is filtered off, the filtrate is evaporated to dryness and the residue is purified by crystallisation or chromatography.

Using this method, numerous hydrogenolyses are carried out, to obtain, inter alia:

a) from 7-benzyl-8-cyclopentyl-3-(2-(p-methoxyphenyl)-ethyl)-1-propylxanthine: 8-cyclopentyl-3-(2-(p-methoxyphenyl)-ethyl)-1-propylxanthine, 70.6% of theory, mp.=208° C.

b) from 1-allyl-7-benzyl-8-cyclopentyl-3-(3-methoxypropyl)-xanthine: 8-cyclopentyl-3-(3-methoxypropyl)-1-propylxanthine, 71.4% of theory, mp.=174°–175° C.

c) from 7-benzyl-8-cyclopentyl-3-(3-(hydroxypropyl)-1-propylxanthine: 8-cyclopentyl-3-(3-hydroxypropyl)-1-propylxanthine, 26.6% of theory, mp.=213°–215° C.

d) from 7-benzyl-8-cyclopentyl-3-(3-(p-methoxyphenyl)-propyl)-1-propylxanthine: 8-cyclopentyl-3-(3-(p-methoxyphenyl)-propyl)-1-propylxanthine, 80.6% of theory, mp.=153°–154° C.

e) with palladium on activated charcoal in methanol/HCl from 7-benzyl-3-(2-carboxyethyl)-8-cyclopentyl-1-propylxanthine: 8-cyclopentyl-3-(2-methoxycarbonylethyl)-1-propylxanthine, 16.3% of theory, mp.=201°–203° C.

f) from 7-benzyl-8-cyclopentyl-3-(3-p-hydroxyphenyl)-propyl))-1-propylxanthine: 8-cyclopentyl-3-(3-(p-hydroxyphenyl)-propyl)-1-propylxanthine, 26.8% of theory, mp.=239°–241° C.

g) from 7-benzyl-8-cyclopentyl-3-(2-(methylaminocarbonyl)-ethyl)-1-propylxanthine: 8-cyclopentyl-3-(2-(methylaminocarbonyl)-ethyl)-1-propylxanthine, 67.7% of theory, mp.=297°–298° C.

h) from 7-benzyl-8-cyclopentyl-3-(2-(3,4,5-trimethoxybenzylaminocarbonyl)-ethyl)-1-propylxanthine: 8-cyclopentyl-3-(2-(3,4,5-trimethoxybenzylaminocarbonyl)-ethyl)-1-propylxanthine, 77.2% of theory, mp.=231°–233° C.

i) from 7-benzyl-8-cyclopentyl-3-(3-(p-methylcarbonyloxyphenyl)-propyl)-1-propylxanthine: 8-cyclopentyl-3-(3-(p-methylcarbonyloxyphenyl)-propyl)-1-propylxanthine, 63.9% of theory, mp.=181°–183° C.

j) from 7-benzyl-8-cyclopentyl-3-(2-(N-morpholinocarbonyl)-ethyl)-1-propylxanthine: 8-cyclopentyl-3-(2-(N-morpholinocarbonyl)-ethyl)-1-propylxanthine, 50% of theory, mp.=169°–171° C.

k) from 7-benzyl-8-cyclopentyl-3-(3-(N-morpholino)-propyl)-1-propylxanthine: 8-cyclopentyl-3-(3-(N-morpholino)-propyl)-1-propylxanthine, 59.7% of theory, mp.=176°–178° C.

l) from 7-benzyl-8-cyclopentyl-3-(2-(2,4,6-trimethoxybenzylaminocarbonyl)-ethyl)-1-propylxanthine: 8-cyclopentyl-3-(2-(2,4,6-trimethoxybenzylaminocarbonyl)-ethyl)-1-propylxanthine, 47.2% of theory, mp.=241°–243° C.

m) from 7-benzyl-8-cyclopentyl-3-(3-(p-(ethoxycarbonylmethyloxy)-phenyl)-propyl)-1-propylxanthine, 8-cyclopentyl-3-(3-(p-(ethoxycarbonylmethyloxy)-phenyl)-propyl)-1-propylxanthine, 77.4% of theory, mp.=141°–143° C.

n) from 7-benzyl-8-cyclopentyl-3-(3-acetoxypropyl)-1-propylxanthine: 8-cyclopentyl-3-(3-acetoxypropyl)-1-propylxanthine, 93.5% of theory, mp.=157°–159° C.

o) from 7-benzyl-8-cyclopentyl-3-(3-hydroxybutyl)-1-propylxanthine: 8-cyclopentyl-3-(3-hydroxybutyl)-1-propylxanthine, 60.0% of theory, mp.=198°–199° C.

p) from 7-benzyl-8-cyclopentyl-3-(3-(p-(2-hydroxyethoxy)-phenyl)-propyl)-1-propylxanthine: 8-cyclopentyl-3-(3-(p-(2-hydroxyethoxy)-phenyl)-propyl) 1-propylxanthine, 59.6% of theory, mp.=168°–169° C.

q) from 7-benzyl-8-cyclopentyl-3-(3-(p-(2-(methylcarbonyloxy)-ethoxy)-phenyl)-propyl)-1-propyl xanthine: 8-cyclopentyl-3-(3-(p-(2-(methylcarbonyloxy)-ethoxy)-phenyl)-propyl)-1-propylxanthine, 48.1% of theory, mp.=139°–140° C.

r) from 7-benzyl-8-cyclopentyl-3-(3-(N-piperidinyl)-propyl)-1-propylxanthine: 8-cyclopentyl-3-(3-(N-piperidinyl)-propyl)-1-propylxanthine, 78.4% of theory, mp.=152°–154° C.

s) from 7-benzyl-8-cyclopentyl-3-(3-(N-pyrrolidinyl)-propyl)-1-propyolxanthine: 8-cyclopentyl-3-(3-(N-pyrrolidinyl)-propyl)-1-propylxanthine, 52.6% of theory, mp.=162°–163° C.

t) from 7-benzyl-8-cyclopentyl-3-(3-(p-(methoxycarbonylmethyloxy)-phenyl)-propyl)-1-propylxanthine: 8-cyclopentyl-3-(3-(p-(methoxycarbonylmethyloxy)-phenyl)-propyl)-1-propylxanthine, 86.5% of theory, $^1$H-NMR (250 MHz, DMSO-$d_6$):$\delta$ (ppm)=7.11 (d, J=8.8 Hz, 2H), 6.79 (d, J=8.8 Hz, 2H), 4.72 (s, 2H), 3.98 (t, J=7.3 Hz, 2H), 3.80 (t, J=7.3 Hz, 2H), 3.69 (s, 3H), 3.13 (m, 1H), 2.55 (m, 2H), 2.07–1.45 (m, 12 H), 0.85 (t, J=7.6 Hz, 3H).

u) from 7-benzyl-8-cyclopentyl-3-(2-methoxyethyl)-1-propylxanthine: 8-cyclopentyl-3-(2-methoxyethyl)-1-propylxanthine, 81.2% of theory, mp.=185° C.

v) from 7-benzyl-3-(2-(cyclohexyl)-ethyl)-8-cyclopentyl-1-propylxanthine: 3-(2-(cyclohexyl)-ethyl)-8-cyclopentyl-1-propylxanthine, mp.=188°–189° C.

w) from 7-benzyl-8-cyclopentyl-3-(2-phenylethyl)-1-propylxanthine: 8-cyclopentyl-3-(2-phenylethyl)-1-propylxanthine, 34.5% of theory, mp.=215°–216° C.

x) from 7-benzyl-8-cyclopentyl-3-(3-(phenyl)-propyl)-1-propylxanthine: 8-cyclopentyl-3-(3-(phenyl)-propyl)-1-propylxanthine, 28.6% of theory, mp.=153° C. (decomposition)

y) from 7-benzyl-3-(3-cyanopropyl)-8-cyclopentyl-1-propylxanthine: 3-(3-cyanopropyl)-8-cyclopentyl-1-propylxanthine, 69.0% of theory, mp.=>300° C.

z) from 7-benzyl-3-(5-cyanopentyl)-8-cyclopentyl-1-propylxanthine: 3-(5-cyanopentyl)-8-cyclopentyl-1-propylxanthine, 21.1% of theory, mp =160° C. (decomposition)

a1) from 3-(3-(aminocarbonyl)-propyl)-7-benzyl-8-cyclopentyl-1-propylxanthine: 3-(3-(aminocarbonyl)-propyl)-8-cyclopentyl-1-propylxanthine, mp=164°–165° C.

Method B:

3.3 mMol of N-benzyl compound are dissolved in 70 ml of absolute methylene chloride. 3.36 g (52.8 mMol) of ammonium formate and 1.32 g of Pearlman-catalyst are added and the suspension is refluxed for 2 hours. After cooling, the mixture is filtered over kieselguhr and the filtrate is evaporated to dryness. If necessary the residue is purified by crystallisation or chromatography.

Numerous hydrogenolyses were carried out using this method, to obtain inter alia:

a) from 7-benzyl-8-cyclopentyl-1-propyl-3-(2-(2-pyridyl)-ethyl)-xanthine: 8-cyclopentyl-1-propyl-3-(2-(2-pyridyl)-ethyl)-xanthine, mp=201°–202° C.

14. Hydrogenation of nitrile groups 3.3 mMol of nitrile derivative are dissolved in 40 ml of methanol and 10.5 ml of 25% aqueous ammonia solution and hydrogenated under pressure in the presence of Raney nickel, optionally with heating, until all the starting compound has reacted.

The following was obtained, for example, using this method:

a) 3-(4-aminobutyl)-8-cyclopentyl-1-propylxanthine, 40.9% of theory, mp.=159°–161° C.

15. Acylation of hydroxy groups 1.3 mMol of hydroxy compound and 0.53 ml (6.5 mMol) of pyridine are dissolved or suspended in 10 ml of absolute methylene chloride. A solution of 1.44 mMol of carboxylic acid chloride in 1 ml of absolute methylene chloride is added dropwise at ambient temperature with stirring and the reaction mixture is stirred until all the starting compound has reacted. The mixture is then extracted with distilled water and dilute hydrochloric acid, the organic phase is dried over sodium sulphate and evaporated to dryness. The residue is purified by crystallisation or by chromatography.

Using this method, the following O-acyl compounds were prepared, inter alia:

a) 8-cyclopentyl-3-(2-(methylcarbonyloxy)-ethyl)-1-propylxanthine, 47% of theory, mp.=149° C.

b) 8-cyclopentyl-3-(2-(p-(methylcarbonyloxy)-phenyl)-ethyl)-1-propylxanthine, 47% of theory, mp.=232° C.

c) 7-benzyl-8-cyclopentyl-3-(3-(p-(methylcarbonyloxy)-phenyl)-propyl-1-propylxanthine, 77.5% of theory, gradually crystallising oil d) 7-benzyl-8-cyclopentyl-3-(3-(methylcarbonyloxy)-propyl)-1-propylxanthine, 98.6% of theory, gradually crystallising oil e) 7-benzyl-8-cyclopentyl-3-(3-(p-(2-(methylcarbonyloxy)-ethoxy)-phenyl)-propyl)-1-propylxanthine, 82.1% of theory, colourless oil

16. Hydrolysis of carboxylic acid esters 0.6 mMol of ester derivative are dissolved in about 4 ml of tetrahydrofuran and mixed with a solution of 0.17 g (4.0 mMol) of lithium hydroxide-hydrate in. 10 ml of distilled water. The reaction mixture is stirred until all the starting substance has reacted, then made alkaline with dilute hydrochloric acid and the product is filtered off or the aqueous phase is extracted with organic solvent. In order to purify it it may be recrystallised or chromatographed.

Using this method, the following compounds were prepared inter alia:

a) from 8-cyclopentyl-3-(3-(p-(ethoxycarbonylmethyloxy)-phenyl)-propyl)-1-propylxanthine: 3-(3-(p-(carboxymethyloxy)-phenyl)-propyl)-8-cyclopentyl-1-propylxanthine, 85.2% of theory, mp.=190°–192° C.

b) from 8-cyclopentyl-3-(2-(methyloxycarbonyl)-ethyl)-1-propylxanthine: 3-(2-carboxyethyl)-8-cyclopentyl-1-propylxanthine, 78.5% of theory, mp.=265°–267° C.

17. Hydrolysis of methoxybenzylamides 1.1 mMol of methoxybenzylamide derivative are suspended or dissolved at 0° C. in 50 ml of absolute methylene chloride. A solution of 5 ml of trifluoroacetic acid in 5 ml of absolute methylene chloride is added dropwise, the mixture is heated to ambient temperature and stirred until all the starting compound has reacted. The reaction mixture is washed with distilled water, the organic phase is dried over sodium sulphate and evaporated to dryness. The crude product is purified by crystallisation or by chromatography.

Using this method, the following compounds are obtained, inter alia:

a) from 8-cyclopentyl-3-(2-(2,4,6-trimethoxybenzylaminocarbonyl)-ethyl)-1-propylxanthine: 3-(2-carbamoylethyl)-8-cyclopentyl-1-propylxanthine, 64.9% of theory, mp.=289°–291° C.

b) from 3-(3-(p-(2,4,6-trimethoxybenzylaminocarbonylmethyloxy)-phenyl)-propyl)-8-cyclopentyl-1-propylxanthine: 3-(3-(p-(carbamoylmethyloxy)-phenyl)-propyl)-8-cyclopentyl-1-propylxanthine, 49.0% of theory, mp.=224°–226° C.

18. Preparation of oximes 2.5 mMol of aldehyde, 0.17 g (2.5 mMol) of hydroxylamine-hydrochloride and 0.13 g (1.3 mMol) of sodium carbonate are mixed into 15 ml of distilled water and stirred together at ambient temperature until all the starting compound has reacted. Methylene chloride is added to the mixture and the solid is removed by suction filtering or the aqueous phase is extracted with methylene chloride. The crude product is purified by crystallisation or by chromatography.

Using this method the following was prepared, for example:

a) from 8-cyclopentyl-3-formylmethyl-1-propylxanthine: 8-cyclopentyl-3-hydroximinoethyl-1-propylxanthine, 64% of theory, mp.=247° C.

19. Oxidation of alcohols into aldehydes or ketones 0.4 mMol of alcohol derivative are stirred together with 180 mg (0.84 mMol) of pyridinium chlorochromate in 5 ml of absolute methylene chloride until all the starting compound has reacted. The reaction mixture is washed with distilled water, the organic phase is dried over sodium sulphate and evaporated to dryness. The crude product is purified by crystallisation or by chromatography.

Using this method, the following was prepared, inter alia:

a) from 8-cyclopentyl-3-(3-hydroxybutyl)-1-propytxanthine: 8-cyclopentyl-3-(3-oxobutyl)-1-propylxanthine, 73.3% of theory, mp.=223°–224° C.

20. Preparation of thioethers 3.6 mol of alkylhalide derivative are dissolved or suspended in a solution of 0.42 g (7.5 mol) of potassium hydroxide in 60 ml of ethanol. 3.6 mMol of substituted thiol are added and the mixture is refluxed until all the starting compound has reacted. It is evaporated to dryness, the residue is mixed with 4N hydrochloric acid and extracted with methylene chloride. The combined organic phases are dried with magnesium sulphate and evaporated to dryness. The residue is purified by crystallisation or by chromatography.

Using this method, the following were prepared, inter alia:

from 8-cyclopentyl-3-(2-iodoethyl)-1-propylxanthine:

a) 8-cyclopentyl-3(-(2-ethylthio)-ethyl)-1-propylxanthine, 71.3% of theory, mp.=144°–145° C.

b) 8-cyclopentyl-3-(2-(2-hydroxyethyl)-thioethyl)-1-propylxanthine, 95% of theory, mp.=160°–161° C.

21. Saponification of nitriles 0.5 mMol of nitrile are suspended or dissolved at 10° C. in 1 ml of 95–97% sulphuric acid. The mixture is stirred for 3.5 hours at ambient temperature, 5 ml of water and 5 ml of methylene chloride are added thereto, the organic phase is separated off and evaporated to dryness. The residue is purified by crystallisation or chromatography. For example, from 7-benzyl-3(3-cyano-propyl)-8-cyclopentyl-1-propylxanthine is obtained: 3-(3-(aminocarbonyl)-propyl)-7-benzyl-8-cyclopentyl-1-propylxanthine, mp.=180°–181° C.

22. Preparation of alkyliodides from alcohols 3.1 mMol of 8-cyclopentyl-3-(2-hydroxyethyl)-1-propylxanthine, 3.1 mMol of tetraiodomethane and 3.1 mMol of triphenylphosphine are mixed in 15 ml of absolute toluene and refluxed for 2 hours. The mixture is diluted with toluene and the organic phase is washed with water and sodium thiosulphate solution. The crystals precipitated are filtered off, the organic phase of the filtrate is separated off, washed with water, dried and evaporated to dryness. The residue and the filtered off crystals are combined, stirred in acetonitrile for 16 hours at ambient temperature and the solid is isolated by filtration. Yield: 1.0 g (77.5% of theory) of 8-cyclopentyl-3-(2-iodoethyl)-1-propyl-xanthine in the form of colourless crystals, mp.=223°–226° C.

23. Oxidation of thioethers into sulphones 0.55 g of neutral aluminium oxide are mixed with 0.11 ml of water and shaken until a fine powder is formed. 8 ml of methylene chloride, 1.0 g (1.65 mMol) of oxone [=2KHSO$_5$ * KHSO$_4$ * K$_2$HSO$_4$] and a solution of 0.2 g (0.55 mMol) of 8-cyclopentyl-3-(2-(2-hydroxyethyl)-thioethyl)-1-propylxanthine in 4 ml of absolute methylene chloride are added successively and the mixture is refluxed for 2 hours with stirring. After cooling, the solids are filtered off, washed thoroughly with methylene chloride and the combined filtrates are evaporated to dryness. The residue is purified by chromatography on silica gel.

0.2 g (91.3% of theory) of 8-cyclopentyl-3-(2-(2-hydroxyethyl)-sulphonylethyl)-1-propyl-xanthine is obtained in the form of colourless crystals mp. 213°–214° C.

24. Synthesis of 8-cyclopentyl-7-benzyl-3-p-methoxy-xanthine 50 g (0.20 mol) of 6-amino-1-p-methoxybenzyl-uracil are added with 17.5 g of NaHCO$_3$ (0.21 mol) of 200 ml of methanol and at 5° C. 11 ml of bromine are slowly added dropwide (vigorous foaming). Then the mixture is stirred for 2 hours in an ice bath. It is suction filtered and washed twice with 150 ml of methanol. Yield: 54.3 g of light yellow crystals (82.2% of theory) 6-amino-5-bromo-1-p-methoxybenzyl-uracil TLC: 95:5 CH$_2$Cl$_2$:CH$_3$OH mp: 245° C. (Decomp.)

121.1 g (0.37 mol) of 6-amino-5-bromo-1-p-methoxybenzyl-uracil are mixed with 396.5 g of benzylamine (3.7 mol) and stirred for 2 hours at 80° C. The mixture is cooled, extracted with 1000 ml of ethanol, cooled and suction filtered. It is then washed with cold ethanol.

Yield: 110.0 g of white crystals (83.6% of theory) 5-amino-5-benzyl-amino-1-p-methoxybenzyl-uracil TLC: 90:10 CH$_2$Cl$_2$.CH$_3$OH mp: 230°–231° C.

110.0 g (0.31 mol) of 5-amino-5-benzyl-amino-1-p-methoxybenzyl-uracil are placed with 52.8 g of 4-dimethylamino-pyridine (0.43 mol) in 1,650 ml of DMF and at 5° C. a solution of 66.0 g of cyclopentancarboxylic acid chloride (0.50 mol) and 165 ml of DMF is added dropwise. The mixture is then stirred at 5°–25° C. for 3 days. It is evaporated down in vacuo, the residue is boiled twice with 700 ml of ethanol, then cooled and suction filtered. Yield: 113.0 g of white crystals (81.3% of theory) 6-cyclopentyl-carbonylamino-5-benzylamino-1-p-methoxybenzyluracil TLC: 95:5 CH$_2$Cl$_2$:CH$_3$OH 113.0 g (0.25 mol) of 6-cyclopentyl-carbonylamino-5-benzylamino-1-p-methoxybenzyluracil are combined with 1,300 ml of H$_2$O and 650 ml of ethanol, 83.3 g of Ca(OH)$_2$ (1.1 mol) and 330 ml of 50% NaOH are added and the resulting mixture is stirred at 100° C. for 20 hours. The mixture is evaporated down in vacuo (only the ethanol is distilled off). The aqueous residue is cooled adjusted to pH 2 with conc. HCl, with ice cooling, and suction filtered. Yield: 93.0 g of beige crystals (86.4% of theory) 7-benzyl-8-cyclopentyl-3-p-methoxybenzyl-xanthine TLC: 90:10 CH$_2$Cl$_2$:CH$_3$OH mp: 172° C.

Analogously to the methods described hereinbefore, the compounds of general formula I listed in the Table were prepared.

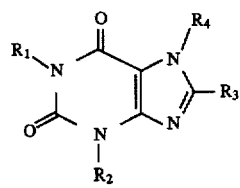

$R_1$=n-propyl, $R_3$=cyclopentyl, $R_4$=hydrogen

| Example No. | $R_2$ | MP. °C. |
|---|---|---|
| 1 | CH$_2$CH$_2$CH$_2$CN | >300 |
| 2 | CH$_2$CH$_2$CH$_2$CH$_2$CH$_2$CN | 160 |
| 3 | CH$_2$CH$_2$OCH$_3$ | 185 |
| 4 | CH$_2$CH$_2$CH$_2$OCH$_3$ | 174–175 |
| 5 | CH$_2$CH$_2$OH | 216 |
| 6 | CH$_2$CH$_2$CH$_2$OH | 213–215 |
| 7 | CH$_2$CH$_2$OCOCH$_3$ | 149 |
| 8 | CH$_2$CH$_2$CH$_2$OCOCH$_3$ | 157–159 |
| 9 | CH$_2$CH$_2$COOH | 265–267 |
| 10 | CH$_2$CH$_2$COOCH$_3$ | 201–203 |
| 11 | CH$_2$CH$_2$CONH$_2$ | 289–291 |
| 12 | CH$_2$CH$_2$CONHCH$_3$ | 297–298 |
| 13 | CH$_2$—CH$_2$CONHCH$_2$—(2,4,5-trimethoxyphenyl with OCH$_3$, OCH$_3$, OCH$_3$) | 221–233 |
| 14 | CH$_2$CH$_2$CO—N(morpholino) | 169–171 |
| 15 | CH$_2$CH$_2$CH(OH)CH$_3$ | 198–199 |
| 16 | CH$_2$CH$_2$COCH$_3$ | 223–224 |
| 17 | CH$_2$CH=NOH | 247 |

-continued

| Example No. | R₂ | MP. °C. |
|---|---|---|
| 18 | CH₂CH₂CH₂CH₂NH₂ | 159–161 |
| 19 | CH₂CH₂CH₂—N(morpholino) | 176–178 |
| 20 | CH₂CH₂CH₂—N(piperidino) | 152–159 |
| 21 | CH₂CH₂—C₆H₅ | 215–216 |
| 22 | CH₂CH₂—C₆H₁₁ | 188–189 |
| 23 | CH₂CH₂CH₂—C₆H₅ | 153 |
| 24 | CH₂CH₂—C₆H₄—OH | 270–272 |
| 25 | CH₂CH₂CH₂—C₆H₄—OH | 239–241 |
| 26 | CH₂CH₂—C₆H₄—OCH₃ | 208 |
| 27 | CH₂CH₂CH₂—C₆H₄—OCH₃ | 153–154 |
| 28 | CH₂CH₂—C₆H₄—OCOCH₃ | 232 |
| 29 | CH₂CH₂CH₂—C₆H₄—OCOCH₃ | 181–183 |
| 30 | CH₂CH₂CH₂—C₆H₄—OCH₂COOH | 190–192 |
| 31 | CH₂CH₂CH₂—C₆H₄—OCH₂COOEt | 141–143 |
| 32 | CH₂CH₂CH₂—C₆H₄—OCH₂CONH₂ | 224–226 |

-continued

| Example No. | R₂ | | MP. °C. |
|---|---|---|---|
| 33 | CH₂CH₂CH₂—⟨C₆H₄⟩—OCH₂OAc | | 139–140 |
| 34 | CH₂CH₂CH₂OCH₃ | R₁ = H | 257–258 |
| 35 | CH₂CH₂CH₂—⟨C₆H₄⟩—OCH₃ | R₁ = H | 292–293 |
| 36 | CH₂CH₂CH₂OCH₃ | R₁ = H<br>R₇ = CH₂Ph | 137–138 |
| 37 | CH₂CH₂—⟨C₆H₄⟩—Cl | R₁ = H | 298–299 |
| 38 | CH₂CH₂OCH₃ | R₁ = H | 293–294 |
| 39 | CH₂CH₂—⟨C₆H₄⟩—OCH₃ | | 256–258 |
| 40 | CH₂—⟨C₆H₄⟩—OCH₃ | R₁ = H | 311 |
| 41 | CH₂—⟨C₆H₄⟩—CN | R₁ = H | >350 |
| 42 | CH₂—⟨C₆H₄⟩—CN | | 265–267 |
| 43 | CH₂—⟨C₆H₄⟩—CH₂NH₂ | | 322 |
| 44 | CH₂—⟨C₆H₄⟩—NO₂ | | 259–260 |
| 45 | CH₂—⟨C₆H₄⟩—OCH₂CH₂OH | | 168–169 |
| 46 | (CH₂)—S—Et | | 144–145 |
| 47 | —(CH₂)—S—(CH₂)₂—OH | | 160–161 |
| 48 | CH₂CH₂CH₂—⟨C₆H₄⟩—OCH₂O | | 168–169 |
| 49 | CH₂CH₂CH₂—N⟨ ⟩ | | 162–163 |

-continued
| Example No. | R₂ | MP. °C. |
|---|---|---|
| 50 | 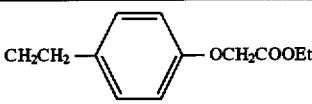 CH₂CH₂—C₆H₄—OCH₂COOEt | 191–193 |
| 51 | 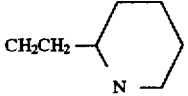 CH₂CH₂-(piperidinyl) | 179–181 |
| 52 | 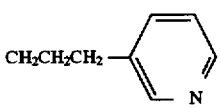 CH₂CH₂CH₂-(3-pyridyl) | 187–189 |
| 53 | 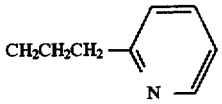 CH₂CH₂CH₂-(2-pyridyl) | 167–168 |
| 54 | CH₂CH₂SO₂CH₂CH₂OCOCH₃ | 171–172 |
| 55 | 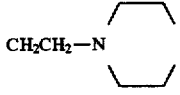 CH₂CH₂—N(morpholinyl) | 162–163 |
| 56 | 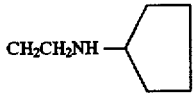 CH₂CH₂NH-cyclopentyl | 141–142 |
| 57 | 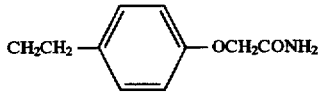 CH₂CH₂—C₆H₄—OCH₂CONH₂ | 231–232 |
| 58 | 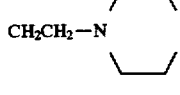 CH₂CH₂—N(thiomorpholinyl) | 255–256 |
| 59 | 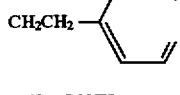 CH₂CH₂-(4-pyridyl) | 201–201 |
| 60 | (CH₂)₃CONH₂ | 264–265 |
| 61 | 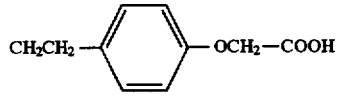 CH₂CH₂—C₆H₄—OCH₂—COOH | 224–226 |
| 62 | 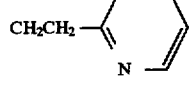 CH₂CH₂-(2-pyridyl) | 195–196 |
| 63 | 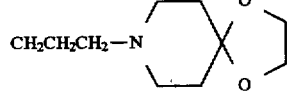 CH₂CH₂CH₂—N(piperidinyl-4-spiro-dioxolane) | 168–196 |
| 64 | 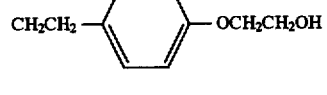 CH₂CH₂—C₆H₄—OCH₂CH₂OH | 231 |

-continued

| Example No. | R₂ | MP. °C. |
|---|---|---|
| 65 | CH₂—CH₂—C₆H₄—COOCH₃ (para) | 235–236 |
| 66 | CH₂CH₂—C₆H₄—COOH (para) | 310–311 |
| 67 | CH₂CH₂CH₂—N(piperidin-4-one) | 196–197 |
| 68 | CH₂CH₂—N(thiomorpholine) | 246–248 |
| 69 | CH₂—CH₂—C₆H₄—OCH₂—CON(CH₃)₂ (para) | 160 |
| 70 | CH₂CH₂SO₂CH₂CH₂OH | 213–214 |
| 71 | CH₂CH₂—C₆H₄—CONH₂ (para) | 265–266 |
| 72 | CH₂CH₂—N(pyrrolidin-3-one) | 188 |
| 73 | CH₂CH₂CH₂—N(4-hydroxypiperidine) | 163–164 |
| 74 | CH₂CH(OH)CH₂OH | 225–226 |
| 75 | CH₂CH₂—C₆H₄—CH₂NHSO₂Me (para) | 210 |
| 76 | CH₂CH₂—C₆H₄—C(O)N(morpholine) (para) | 214–215° C. |
| 77 | CH₂CH₂CH₂—N(piperazine)N—COCH₃ | 169–170 |
| 78 | CH₂CH₂CH₂—N(piperazine)N—CH₃ | 162–163 |
| 79 | CH₂CH₂CH₂—N(piperazine)N—H | 253–254 |

-continued

| Example No. | R$_2$ | MP. °C. |
|---|---|---|
| 80 | CH$_2$CH$_2$CH$_2$—(piperidine-N-COCH$_3$) | 136–137 |
| 81 | CH$_2$CH$_2$CH$_2$—(piperidine-N-SO$_2$CH$_3$) | 216–217 |
| 82 | CH$_2$CH$_2$CH$_2$—(piperidine-N-H) | 146–147 |
| 83 | CH$_2$CH$_2$CH$_2$—NH—(cyclopentyl) | 218–220 |
| 84 | (R)—CH$_2$CH$_2$CH(OH)CH$_3$ | 198–199 |
| 85 | CH$_2$CH$_2$—(C$_6$H$_4$)—SO$_2$NH$_2$ | 307–308 |
| 86 | CH$_2$CH$_2$—(C$_6$H$_4$)—SO$_2$NHCH$_3$ | 225–226 |
| 87 | CH$_2$CH$_2$—(C$_6$H$_4$)—SO$_2$N(CH$_3$)$_2$ | 190–191 |
| 88 | CH$_2$CH$_2$NHCOCH$_3$ | 268–269 |
| 89 | CH$_2$CH$_2$OCH$_2$CH$_2$—N(piperazine)N—SO$_2$CH$_3$ | 160 |
| 90 | CH$_2$CH$_2$NH—CO—(pyridyl) | 254–255 |
| 91 | CH$_2$CH$_2$NH—CO—(piperidine N—H) | 267–268 |

Me = Methyl
Et = Ethyl
Ph = Phenyl

The compounds of general formula I may be used on their own or in conjunction with other active substances according to the invention, possibly combined with other pharmacologically active substances. Suitable forms include, for example, tablets, capsules, suppositories, solutions, syrups, emulsions, aerosols or dispersible powders. Tablets may be produced, for example, by mixing the active substance or substances with known excipients, e.g. inert diluents such as calcium carbonate, calcium phosphate or lactose, disintegrants such as corn starch or alginic acid, binders such as starch or gelatine, lubricants such as magnesium stearate or talc and/or agents for obtaining delayed release, such as carboxymethylcellulose, cellulose acetate phthalate or polyvinylacetate. The tablets may also consist of several layers.

Coated tablets may be produced analogously by coating cores made in the same way as the tablets with substances conventionally used for tablet coatings, e.g. collidone or shellac, gum arabic, talc, titanium dioxide or sugar. In order to obtain delayed release or avoid incompatibilities, the core may also consist of several layers. Similarly, the tablet coating may consist of several layers to achieve delayed release, whilst the excipients mentioned for the tablets may be used.

Syrups containing the active substances or combinations of active substances according to the invention may additionally contain a sweetener such as saccharin, cyclamate, glycerol or sugar as well as a flavour enhancer, e.g. a flavouring such as vanillin or orange extract. They may also contain suspension adjuvants thickeners such as sodium carboxymethylcellulose, wetting agents, e.g. condensation products of fatty alcohols with ethylene oxide or preservatives such as p-hydroxybenzoates.

Injectable solutions are produced in the usual way, e.g. by adding preservatives such as p-hydroxybenzoates or stabilisers such as alkali metal salts of ethylene diamine tetraacetic acid, and are then transferred into injection vials or ampoules.

Capsules containing one or more active substances or combinations of active substances may be prepared for example by mixing the active substances with inert carriers such as lactose or sorbitol and encapsulating them in gelatine capsules.

Suitable suppositories may be produced for example by mixing with carriers provided for this purpose, such as neutral fats or polyethyleneglycol or derivatives thereof.

A therapeutically effective daily dose is between 1 and 800 mg, preferably 10–300 mg per adult.

The following Examples illustrate the present invention without restricting their scope:

Examples of Pharmaceutical Formulations

| A) | Tablets | per tablet |
|---|---|---|
| | Active substance | 100 mg |
| | Lactose | 140 mg |
| | Corn starch | 240 mg |
| | Polyvinylpyrrolidone | 15 mg |
| | Magnesium stearate | 5 mg |
| | | 500 mg |

The finely ground active substance, lactose and some of the corn starch are mixed together. The mixture is screened, then moistened with a solution of polyvinylpyrrolidone in water, kneaded, moist-granulated and dried. The granules, the remaining corn starch and the magnesium stearate are screened and mixed together. The mixture is compressed to form tablets of a suitable shape and size.

| B) | Tablets | per tablet |
|---|---|---|
| | Active substance | 80 mg |
| | Corn starch | 190 mg |
| | Lactose | 55 mg |
| | Microcrystalline cellulose | 35 mg |
| | Polyvinylpyrrolidone | 15 mg |
| | Sodium-carboxymethylstarch | 23 mg |
| | Magnesium stearate | 2 mg |
| | | 400 mg |

The finely ground active substance, some of the corn starch, lactose, microcrystalline cellulose and polyvinylpyrrolidone are mixed together, the mixture is screened and processed with the remaining corn starch and water to form granules which are dried and screened. The sodium carboxymethyl starch and the magnesium stearate are added, mixed together and the mixture is compressed to form tablets of a suitable size.

What is claimed is:

1. A compound of formula

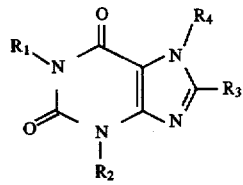

wherein $R_1$ cannot be the same as $R_2$ and:

$R_2$ is hydrogen, $C_1$-$C_6$-alkyl, $C_3$-$C_6$-alkenyl, or $C_3$-$C_6$-alkynyl;

$R_2$ is a $C_1$-$C_8$-alkyl-, $C_2$-$C_8$-alkenyl- or $C_2$-$C_8$-alkynyl-group which is substituted by —CN, —CH$_2$NR$_6$R$_7$, —OH, —OR$_8$, —NR$_6$R$_7$, —NHCOR$_8$, —NHCONR$_6$R$_7$, halogen, —OCOR$_8$, —OCH$_2$COOH, —OCH$_2$COOR$_8$, —SO$_2$R$_5$, —SR$_5$, —NHCONH phenyl,- OCH$_2$CONR$_6$R$_7$, —OCH$_2$CH$_2$OH, —SO$_2$CH$_2$CH$_2$OCOR$_8$, —OCH$_2$CH$_2$NR$_6$R$_7$, —SO$_2$CH$_2$CH$_2$OH, —CONHSO$_2$R$_8$, —CH$_2$CONHSO$_2$R$_8$, —OCH$_2$CH$_2$OR$_8$, —COOH, —COOR$_8$, —CONR$_6$R$_7$, —CHO, —SR$_8$, —SOR$_8$, —SO$_2$R$_8$, —SO$_3$H, —SO$_2$NR$_6$R$_7$, —OCH$_2$CH$_2$OCOR$_8$, —CH=NOH, —CH=NOR$_8$, —COR$_9$, —CH(OH)R$_9$, —CH(OR$_8$)$_2$, —CH=CHR$_{10}$, —OCONR$_6$R$_7$,

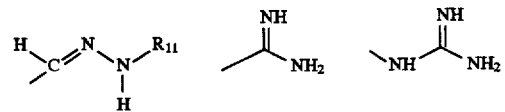

or by 1,3-dioxolane or 1,3-dioxane which is optionally mono- or polysubstituted by methyl; or $R_2$ is phenyl-$C_1$-$C_6$-alkylene, phenyl-$C_2$-$C_6$-alkenylene or phenyl-$C_2$-$C_6$-alkynylene, in which the phenyl ring is optionally substituted, either directly or via a $C_{1-4}$-alkylene group, with one or more of the following groups:

—C$_1$-C$_3$-alkyl, —CN, —CH$_2$NR$_6$R$_7$, —OH, —OR$_8$; —CH$_2$NHSO$_2$R$_8$, —NHCOR$_8$, —NHCONR$_6$R$_7$, halogen, —OCOR$_8$, —OCH$_2$COOH, —OCH$_2$COOR$_8$, —CH$_2$OCOR$_8$, —SO$_2$R$_5$, —OCH$_2$CONR$_6$R$_7$, —OCH$_2$CH$_2$OH, —OCH$_2$CH$_2$NR$_6$R$_7$, —CONHSO$_2$R$_8$, —OCH$_2$CH$_2$OR$_8$, —COOH, —COOR$_8$, —CF$_3$, cyclopropyl, —CONR$_6$R$_7$, —CH$_2$OH, —CH$_2$OR$_8$, —CHO, —SR$_8$, —SOR$_8$, —SO$_2$R$_8$, —SO$_3$H, —SO$_2$NR$_6$R$_7$, —OCH$_2$CH$_2$OCOR$_8$, —CH=NOH, —CH=NOR$_8$, —COR$_9$, —CH(OH)R$_9$, —CH(OR$_8$)$_2$, —NHCOOR$_8$, —CH$_2$CONHSO$_2$R$_8$, —CH=CH—R$_{10}$, —OCONR$_6$R$_7$, —CH$_2$OCONR$_6$R$_7$, —CH$_2$CH$_2$OCONR$_6$R$_7$,

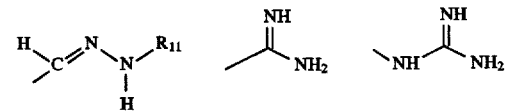

or by 1,3-dioxolane or 1,3-dioxane which is optionally mono- or polysubstituted by methyl; or $R_2$ is $C_3$-$C_7$-cycloalkyl-$C_1$-$C_6$-alkylene-, $C_3$-$C_7$-cycloalkyl-$C_2$-$C_6$-alkenylene-, or $C_3$-$C_7$-cycloalkyl- $C_2$-$C_6$-alkynylene-, in which the cycloalkyl group may optionally be substituted, either directly or via a $C_{1-4}$-alkylene group, by —CN, —CH$_2$NR$_6$R$_7$, =O, —OH, —OR$_8$, —NR$_6$R$_7$, —NHCOR$_8$, —NHCONR$_6$R$_7$, halogen, —OCOR$_8$, —OCH$_2$COOH, —OCH$_2$COOR$_8$, —CH$_2$OCOR$_8$, —SO$_2$R$_5$, —OCH$_2$CONR$_6$R$_7$, —OCH$_2$CH$_2$OH, —OCH$_2$CH$_2$NR$_6$R$_7$, —OCH$_2$CH$_2$OR$_8$, —COOH, —COOR$_8$, —CONR$_6$R$_7$, —CH$_2$OH, —CH$_2$OR$_8$, —CHO, —SR$_8$, —SOR$_8$, —SO$_2$R$_8$, —SO$_3$H, —SO$_2$NR$_6$R$_7$, —OCH$_2$CH$_2$OCOR$_8$, —CH=NOH, —CH=NOR$_8$, —COR$_9$, —CH(OH)R$_9$, —CONHSO$_2$R$_8$, —CH(OR$_8$)$_2$, —NHCOOR$_8$, —CH=CHR$_{10}$, —OCONR$_6$R$_7$, —CH$_2$OCONR$_6$R$_7$, —CH$_2$CH$_2$OCONR$_6$R$_7$,

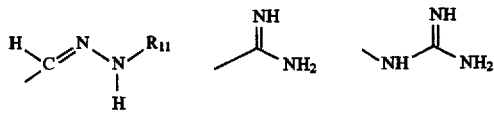

or by 1,3-dioxolane or 1,3-dioxane which is optionally mono- or polysubstituted by methyl; or R$_2$ is a group
A—C$_1$-C$_6$-alkylene-, A—C$_2$-C$_6$-alkenylene, A—C$_2$-C$_6$-alkynylene, A—CONH—C$_1$-C$_6$-alkylene-, A—CONH—C$_2$-C$_6$-alkenylene- or A—CONH—C$_2$-C$_6$-alkynylene-, A—NHCO—C$_1$-C$_6$-alkylene, A—NHCO—C$_2$-C$_6$-alkenylene, A—NHCO—C$_2$-C$_6$ alkynylene, wherein A is a C-linked 5- or 6-membered heterocyclic ring selected from the group consisting of tetrahydrofuran, γ-butyrolactone, α-pyran, γ-pyran, tetrahydropyran, pyrrole, pyrroline, pyrrolidine, piperazine, morpholine, thiomorpholine, imidazole, imidazoline, imidazolidine, pyrazole, pyrazoline, triazole, tetrazole, oxazole, oxadiazole, and pyrazolidine, wherein the heterocyclic ring may optionally be mono- or polysubstituted by $C_1$-$C_4$-alkyl, halogen, —OR$_8$, —CN, —NO$_2$, —NH$_2$, —CH$_2$NR$_6$R$_7$, —OH, =O, —COOH, —SO$_3$H, —COOR$_8$, —CONR$_6$R$_7$, —COR$_9$, —SO$_2$—R$_8$, —CONR$_6$R$_7$ or

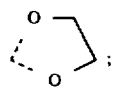

R$_3$ is $C_3$-$C_7$-cycloalkyl, optionally substituted by =O, —OH, —OR$_8$, —OCOR$_8$, or R$_3$ is phenyl, which is optionally substituted by —OH, halogen, —OR$_8$, $C_1$-$C_4$-alkyl, —NH$_2$, —COOH, —SO$_3$H, —COOR$_8$, —OCH$_2$COOR$_8$, —CN, or —OCH$_2$CONR$_6$R$_7$, or R$_3$ is a norbornane-, norbornene-, adamantane- or noradamantane or a $C_3$-$C_6$-dicycloalkylmethyl group; or R$_3$ is —CH=CH-phenyl, wherein the phenyl ring is mono- or polysubstituted by methoxy, hydroxy or halogen; or R$_3$ is a [3.3.0]-bicyclooctane; or R$_3$ is a C-linked piperidine or furan;

R$_4$ is hydrogen, methyl or benzyl, in which the benzyl group may be substituted by 1-3 methoxy groups;

CH$_3$OCH$_2$— CH$_3$SCH$_2$—,

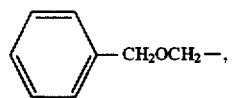

pivaloyloxymethyl or —CH$_2$CH=CH$_2$;

R$_5$ is $C_1$-$C_4$-alkyl, optionally substituted by —OH, —OCOR$_8$, —NH$_2$, —NR$_6$R$_7$ or —NHCOR$_8$, or R$_5$ is —CH$_2$CH$_2$OH, —CH$_2$CH$_2$OCOR$_8$, —CH$_2$CH$_2$CH$_2$OH; or —CH$_2$CH$_2$CH$_2$OCOR$_8$;

R$_6$ is hydrogen, a $C_3$-$C_6$-cycloalkyl group, optionally substituted by $C_1$-$C_4$ alkyl, hydroxy or halogen, a branched or unbranched alkyl-, alkenyl- or alkynyl group having up to 10 carbon atoms, which may optionally be substituted by hydroxy, phenyl, amino, or $C_1$-$C_8$- alkoxy; or R$_6$ is —(CH$_2$)$_m$—NHCOOR$_8$ (wherein m=1, 2, 3 or 4);

R$_7$ is hydrogen, a $C_3$-$C_6$-cycloalkyl group, optionally substituted by $C_1$-$C_4$ alkyl, hydroxy or halogen, a branched or unbranched alkyl-, alkenyl-, or alkynyl group having up to 10 carbon atoms, which may optionally be substituted by hydroxy, phenyl, amino, or $C_1$-$C_8$-alkoxy, or R$_7$ is —(CH$_2$)$_m$—NHCOOR$_8$ (wherein m=1, 2, 3 or 4); or R$_6$ and R$_7$ together with the nitrogen atom form a saturated or unsaturated 5- or 6-membered heterocyclic ring selected from the group consisting of pyrrole, pyrroline, pyrrolidine, N-benzylpiperazine, morpholine, thiomorpholine, imidazole, imidazoline, imidazolidine, pyrazole, pyrazoline, and pyrazolidine wherein the hetrocyclic ring may be substituted by a branched or unbranched $C_{1-4}$-alkyl group, or may carry one of the following groups:
—(CH$_2$)$_n$—NH$_2$, —(CH$_2$)$_n$—NH—$C_1$-$C_4$-alkyl, —(CH$_2$)$_n$—N($C_1$-$C_8$-alkyl)$_2$, or —(CH$_2$)$_n$—NHCOOR$_8$, (wherein n=2, 3 or 4), =O, halogen, —OR$_8$, —CN, —NO$_2$, —NH$_2$, —OH, —COOH, —SO$_3$H, —COOR$_8$, or —SO$_2$R$_8$;

R$_8$ is hydrogen, $C_1$-$C_4$-alkyl, $C_2$-$C_4$-alkenyl, $C_2$-$C_4$-alkynyl, or a benzyl- or phenyl-group which is optionally mono- or polysubstituted by —OCH$_3$;

R$_9$ is $C_1$-$C_4$-alkyl, $C_2$-$C_4$-alkenyl, C2-C4-alkynyl, or $C_3$-$C_6$-cycloalkyl;

R$_{10}$ is —COOR$_8$, —CH$_2$OR$_8$, —CONR$_6$R$_7$, hydrogen, $C_1$-$C_3$-alkyl, or —CH$_2$NR$_6$R$_7$;

R$_{11}$ is hydrogen, phenyl, or —CH$_3$;

optionally in the form of the racemates, the enantiomers, the diastereomers and the mixtures thereof and optionally in the form of the pharmacologically acceptable salts thereof.

2. The compound as recited in claim 1 wherein

R$_1$ is methyl, ethyl, n-butyl, allyl, or n-propyl;

R$_2$ is a $C_2$-alkyl or an unbranched $C_3$-alkyl group which is substituted by —CN, —CH$_2$NR$_6$R$_7$, —OH, —OR$_8$, —NR$_6$R$_7$, —NHCOR$_8$, —NHCONR$_6$H, halogen, —OCOR$_8$, —OCH$_2$COOH, —OCH$_2$COOR$_8$, —SR$_5$, —SO$_2$R$_5$, —OCH$_2$CONR$_6$R$_7$, —OCH$_2$CH$_2$OH, —OCH$_2$CH$_2$NR$_6$R$_7$, —CONHSO$_2$R$_8$, —CH$_2$CONHSO$_2$R$_8$, —OCH$_2$CH$_2$OR$_8$, —COOH, —COOR$_8$, —CONR$_6$R$_7$, —CHO, —SR$_8$, —SO$_2$R$_8$, —SO$_3$H, —SO$_2$NR$_6$R$_7$, —OCH$_2$CH$_2$OCOR$_8$, =NOH, =NOR$_8$, —COR$_9$, —CH(OH)R$_9$, —CH=CHR$_{10}$, —OCONR$_6$H,

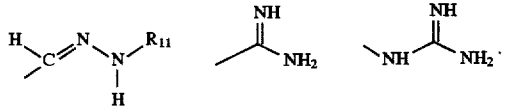

or by 1,3-dioxolane or 1,3-dioxane optionally mono- or polysubstituted by methyl; or R$_2$ is a benzyl-, phenethyl- or phenylpropyl group which is substituted by one of the following groups:
—C$_1$–C$_3$-alkyl, —CN, —CH$_2$NR$_6$R$_7$, —OH, —OR$_8$, —NHCOR$_8$, —NHCONR$_6$R$_7$, halogen, —OCOR$_8$, —OCH$_2$COOH, —OCH$_2$COOR$_8$, —CH$_2$OCOR$_8$, —SO$_2$R$_5$, —OCH$_2$—CONR$_6$R$_7$, —OCH$_2$CH$_2$OH, —CH$_2$CONHSO$_2$R$_8$, —OCH$_2$CH$_2$NR$_6$R$_7$, —CONHSO$_2$R$_8$, —OCH$_2$CH$_2$OR$_8$, —COOH, —COOR$_8$, —CF$_3$, cyclopropyl, —CONR$_6$R$_7$, —CH$_2$OH, —CH$_2$OR$_8$, —CHO, —SR$_8$, —SOR$_8$, —SO$_2$R$_8$, —SO$_3$H, —SO$_2$NR$_6$R$_7$, —OCH$_2$CH$_2$OCOR$_8$, —CH=NOH, —CH=NOR$_8$, —COR$_9$, —CH(OH)R$_9$, —CH(OR$_8$)$_2$, —NHCOOR$_8$, —CH=CHR$_{10}$, —OCONR$_6$R$_7$, —CH$_2$OCONR$_6$R$_7$, —CH$_2$CH$_2$OCONR$_6$R$_7$,

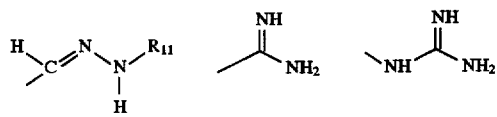

or by 1,3-dioxolane or 1,3 -dioxane optionally mono- or polysubstituted by methyl, and where R$_2$ is OR$_8$, the phenyl group may be trisubstituted; or R$_2$ is a C$_3$-, C$_4$-, C$_5$- or C$_6$-cycloalkyl-C$_2$–C$_3$-alkylene group, wherein the cycloalkyl group is optionally monosubstituted by —CN, —CH$_2$NR$_6$R$_7$, =O, —OH, —OR$_8$, —NR$_6$R$_7$, —NHCOR$_8$, —NHCONR$_6$R$_7$, halogen, —OCOR$_8$, —OCH$_2$COOH, —OCH$_2$COOR$_8$, —CH$_2$OCOR$_8$, —SO$_2$R$_5$, —OCH$_2$CONR$_6$R$_7$, —OCH$_2$CH$_2$OH, —OCH$_2$CH$_2$NR$_6$R$_7$, —OCH$_2$CH$_2$OR$_8$, —COOH, —COOR$_8$, —CONR$_6$R$_7$, —CH$_2$OH, —CH$_2$OR$_8$, —CHO, —SR$_8$, —SOR$_8$, —SO$_2$R$_8$, —SO$_3$H, —SO$_2$NR$_6$R$_7$, —OCH$_2$CH$_2$OCOR$_8$, —CH=NOH, —CH=NOR$_8$, —COR$_9$, —CH(OH)R$_9$, —CH(OR$_8$)$_2$, —NHCOOR$_8$, —CONHSO$_2$R$_8$ —CH=CHR$_{10}$, —OCONR$_6$R$_7$, —CH$_2$OCONR$_6$R$_7$, —CH$_2$—CH$_2$OCONR$_6$R$_7$,

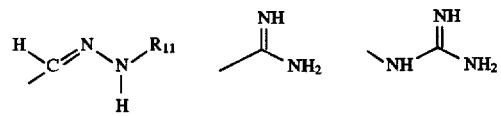

or by 1,3-dioxolane or 1,3-dioxane optionally mono- or polysubstituted by methyl; or R$_2$ is a group
A—CH$_2$—, A—CH$_2$CH$_2$— A—CH$_2$CH$_2$CH$_2$—, A—CONHCH$_2$—, A—CONHCH$_2$CH$_2$—, or A—CONHCH$_2$CH$_2$CH$_2$—,
wherein A is a C- linked 5- or 6-membered heterocyclic ring selected from the group consisting of tetrahydrofuran, tetrahydrofuranone, γ-butyrolactone, α-pyran, γ-pyran, tetrahydropyran, pyrrole, pyrroline, pyrrolidine, piperazine, morpholine, thiomorpholine, imidazole, imidazoline, imidazolidine, pyrazole, pyrazoline, triazole, tetrazole, oxazole, oxadiazole, and pyrazolidine, which may optionally be mono- or polysubstituted by C$_{1-4}$-alkyl, =O, —OH, —COR$_9$, —SO$_2$R$_8$, —NH$_2$, —COOR$_8$, —CONR$_6$R$_7$, —OR$_8$, halogen, —CN, —NO$_2$, —CH$_2$NR$_6$R$_7$, —COOH, —SO$_3$H, —COR$_9$; or

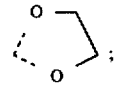

R$_3$ is C$_3$–C$_7$-cycloalkyl, optionally substituted by =O, —OH, —OR$_8$, or —OCOR$_8$; or R$_3$ is phenyl, which is optionally substituted by —OH, halogen, —OR$_8$, C$_1$–C$_4$-alkyl, —NH$_2$, —COOH, —SO$_3$H, —COOR$_8$, —OCH$_2$COOR$_8$, —CN, or —OCH$_2$CONR$_6$R$_7$; or R$_3$ is a norbornane-, norbornene-, adamantane- or noradamantane or a C$_3$–C$_6$-dicycloalkylmethyl group; or R$_3$ is —CH=CH-phenyl, wherein the phenyl ring is mono- or polysubstituted by methoxy, hydroxy or halogen; or R$_3$ is a [3.3.0]-bicyclooctane; or R$_3$ is a C-linked piperidine or furan;

R$_4$ is hydrogen, methyl or benzyl, in which the benzyl group may be substituted by 1–3 methoxy groups; CH$_3$OCH$_2$— CH$_3$SCH$_2$—,

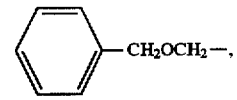

pivaloyloxymethyl or —CH$_2$CH=CH$_2$;

R$_5$ is C$_1$–C$_4$-alkyl, optionally substituted by —OH, —OCOR$_8$, —NH$_2$, —NR$_6$R$_7$ or —NHCOR$_8$; or R$_5$ represents —CH$_2$CH$_2$OH, —CH$_2$CH$_2$OCOR$_8$, —CH$_2$CH$_2$CH$_2$OH, or —CH$_2$CH$_2$CH$_2$OCOR$_8$;

R$_6$ is hydrogen, a C$_3$–C$_6$-cycloalkyl group optionally substituted by C$_1$–C$_4$ alkyl, hydroxy or halogen, a branched or unbranched alkyl-, alkenyl- or alkynyl group having up to 10 carbon atoms, which may optionally be substituted by hydroxy, phenyl, amino, or C$_1$–C$_8$-alkoxy; or R$_6$ is —(CH$_2$)$_m$—NHCOOR$_8$ (wherein m=1, 2, 3 or 4);

R$_7$ is hydrogen, a C$_3$–C$_6$-cycloalkyl group, optionally substituted by C$_1$–C$_4$ alkyl, hydroxy or halogen, a branched or unbranched alkyl-, alkenyl- or alkynyl group having up to 10 carbon atoms, which may optionally be substituted by hydroxy, phenyl, amino, or, C$_1$–C$_8$-alkoxy; or R$_7$ is —(CH$_2$)$_m$—NHCOOR$_8$ (wherein m=1, 2, 3 or 4); or R$_6$ and R$_7$ together with the nitrogen atom form a saturated or unsaturated 5- or 6-membered heterocyclic ring selected from the group consisting of pyrrole, pyrroline, pyrrolidine, N-benzylpiperazine, morpholine, thiomorpholine, imidazole, imidazoline, imidazolidine, pyrazole, pyrazoline, and pyrazolidine wherein the heterocyclic ring may be substituted by a branched or unbranched C$_{1-4}$-alkyl group, or may carry one of the following groups:
—(CH$_2$)$_n$—NH$_2$, —(CH$_2$)$_n$NH—C$_1$–C$_4$-alkyl, —(CH$_2$)$_n$—N(C$_1$–C$_8$-alkyl)$_2$, —(CH$_2$)$_n$—NHCOOR$_8$, (wherein n=2, 3 or 4,), =O, halogen, —OR$_6$, —CN, —NO$_2$, —NH$_2$, =OH, =COOH, —SO$_3$H, —COOR$_8$, or —SO$_2$R$_8$, R$_8$ is hydrogen, C$_1$–C$_4$-alkyl, C$_2$–C$_4$-alkenyl, C$_2$–C$_4$-alkynyl, or a benzyl- or phenyl-group which is optionally mono- or polysubstituted by —OCH$_3$;

R$_9$ is C$_1$–C$_4$-alkyl, C$_2$–C$_4$-alkenyl, C$_2$–C$_4$-alkynyl, or C$_3$–C$_6$-cycloalkyl, R$_{10}$ is —COOR$_8$, —CH$_2$OR$_8$, —CONR$_6$R$_7$, hydrogen, C$_1$–C$_3$-alkyl, or —CH$_2$NR$_6$R$_7$;

R$_{11}$ is hydrogen, phenyl, or —CH$_3$;

optionally in the form of the racemates, the enantiomers, the diastereomers and the mixtures thereof and optionally the pharmacologically acceptable salts thereof.

3. The compound as recited in claim 2

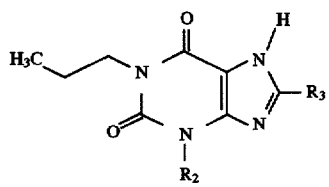

wherein R$_3$ is a group selected from the groups

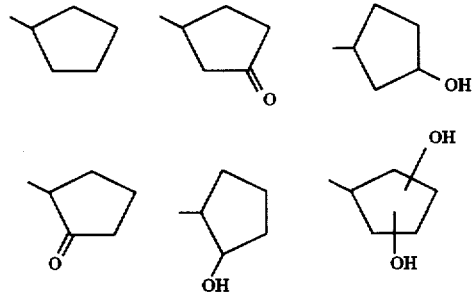

optionally in the form of the racemates, the enantiomers, the diastereomers and the mixtures thereof and optionally the pharmacologically acceptable salts thereof.

4. The compound as recited in claim 1 wherein R$_2$ is an unbranched C$_2$–C$_3$-alkyl group which is substituted by —CN, —OH, —COOH, —COOR$_8$, —COOCH$_3$, —COOC$_2$H$_5$, —OCOCH$_3$, —OCOC$_2$H$_5$, —CONR$_6$R$_7$, =NOH, or —NR$_6$R$_7$.

5. The compound as recited in claim 1 wherein R$_2$ is A—C$_1$–C$_3$-alkylene-, A—CONH—C$_1$–C$_3$-alkylene, or A—NHCO—C$_1$–C$_3$-alkylene.

6. The compound as recited in claim 1, wherein R$_3$ is a group selected from the following

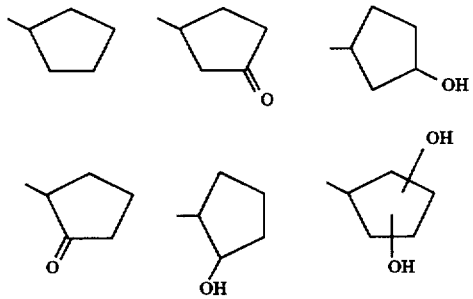

and

R$_2$ is —CH$_2$CH$_2$OH, —CH$_2$CH$_2$OCOCH$_3$, —(CH$_2$)$_3$OCOCH$_3$, —(CH$_2$)$_3$OCH$_3$, —CH$_2$CH$_2$COCH$_3$, —CH$_2$CH$_2$CH(OH)CH$_3$, —CH$_2$CH$_2$COOCH$_3$, —CH$_2$CH$_2$CONH$_2$, —(CH$_2$)$_3$CONH$_2$, —CH$_2$CH=NOH, —(CH$_2$)$_3$CN, —CH$_2$CH$_2$SCH$_2$CH$_3$, —CH$_2$CH$_2$SCH$_2$CH$_2$OH, —CH$_2$CH$_2$SO$_2$CH$_2$CH$_2$OH, —CH$_2$CH$_2$SO$_2$CH$_2$CH$_2$OCOCH$_3$, A—(CH$_2$)$_2$— or A—(CH$_2$)$_3$—;

optionally in the form of the racemates, the enantiomers, the diastereomers and the mixtures thereof and optionally the pharmacologically acceptable salts thereof.

7. The compound as recited in claim 6, wherein R$_3$ is an unsubstituted cyclopentyl group.

8. A compound of formula

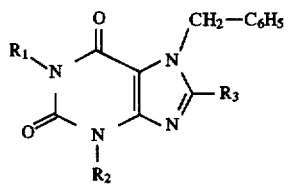

wherein

R$_1$ is hydrogen, C$_1$–C$_6$-alkyl, C$_3$–C$_6$-alkenyl, or C$_3$–C$_6$-alkynyl;

R$_2$ is a C$_1$–C$_8$-alkyl-, C$_2$–C$_8$-alkenyl- or C$_2$–C$_8$-alkynyl-group which is substituted by —CN, —CH$_2$NR$_6$R$_7$, —OH, —OR$_8$, —NR$_6$R$_7$, —NHCOR$_8$, —NHCONR$_6$R$_7$, halogen, —OCOR$_8$, —OCH$_2$COOH, —OCH$_2$COOR$_8$, —SO$_2$R$_5$, —SR$_5$, —NHCONH-phenyl, —OCH$_2$CONR$_6$R$_7$, —OCH$_2$CH$_2$OH, —SO$_2$CH$_2$CH$_2$OCOR$_8$, —OCH$_2$CH$_2$NR$_6$R$_7$, —SO$_2$CH$_2$CH$_2$OH, —CONHSO$_2$R$_8$, —CH$_2$CONHSO$_2$R$_8$, —OCH$_2$CH$_2$OR$_8$, —COOH, —COOR$_8$, —CONR$_6$R$_7$, —CHO, —SR$_8$, —SOR$_8$, —SO$_2$R$_8$, —SO$_3$H, —SO$_2$NR$_6$R$_7$, —OCH$_2$CH$_2$OCOR$_8$, —CH=NOH, —CH=NOR$_8$, —COR$_9$, —CH(OH)R$_9$, —CH(OR$_8$)$_2$, —CH=CHR$_{10}$, OCONR$_6$R$_7$,

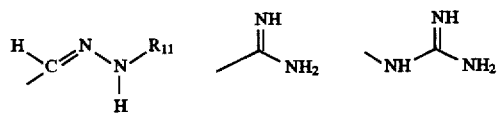

or by 1,3-dioxolane or 1,3-dioxane which is optionally mono- or polysubstituted by methyl; or R$_2$ is phenyl-C$_1$–C$_6$-alkylene, phenyl-C$_2$–C$_6$-alkenylene or phenyl-C$_2$–C$_6$-alkynylene, in which the phenyl ring is optionally substituted, either directly or via a C$_1$–C$_4$-alkylene group, with one or more of the following groups:

—C$_1$–C$_3$-alkyl, —CN, —CH$_2$NR$_6$R$_7$, —OH, —OR$_8$, —CH$_2$NHSO$_2$R$_8$, —NHCOR$_8$, —NHCONR$_6$R$_7$, halogen, —OCOR$_8$, —OCH$_2$COOH, —OCH$_2$COOR$_8$, —CH$_2$OCOR$_8$, —SO$_2$R$_5$, —OCH$_2$CONR$_6$R$_7$, —OCH$_2$CH$_2$OH, —OCH$_2$CH$_2$NR$_6$R$_7$, —CONHSO$_2$R$_8$, —OCH$_2$CH$_2$OR$_8$, —COOH, —COOR$_8$, —CF$_3$, cyclopropyl, —CONR$_6$R$_7$, —CH$_2$OH, —CH$_2$OR$_8$, —CHO, —SR$_8$, —SOR$_8$, —SO$_2$R$_8$, —SO$_3$H, —SO$_2$NR$_6$R$_7$, —OCH$_2$CH$_2$OCOR$_8$, —CH=NOH, —CH=NOR$_8$, —COR$_9$, —CH(OH)R$_9$, —CH(OR$_8$)$_2$, —NHCOOR$_8$, —CH$_2$CONHSO$_2$R$_8$, —CH=CHR$_{10}$, —OCONR$_6$R$_7$, —CH$_2$OCONR$_6$R$_7$, —CH$_2$CH$_2$OCONR$_6$R$_7$, or by 1,3-dioxolane or 1,3-dioxane which is optionally mono- or polysubstituted by methyl; or $R_2$ is $C_3-C_7$-cycloalkyl-$C_1-C_6$-alkylene-, $C_3-C_7$-cycloalkyl-$C_2-C_6$-alkenylene-, $C_3-C_7$-cycloalkyl-$C_2-C_6$-alkynylene-, in which the cycloalkyl group may optionally be substituted, either directly or via a $C_{1-4}$-alkylene group, by —CN, —CH$_2$NR$_6$R$_7$, =O, —OH, —OR$_8$, —NR$_6$R$_7$, —NHCOR$_8$, —NHCONR$_6$R$_7$, halogen, —OCOR$_8$, —OCH$_2$COOH, —OCH$_2$COOR$_8$, —CH$_2$OCOR$_8$, —SO$_2$R$_5$, —OCH$_2$CONR$_6$R$_7$, —OCH$_2$CH$_2$OH, —OCH$_2$CH$_2$NR$_6$R$_7$, —OCH$_2$CH$_2$OR$_8$, —COOH, —COOR$_8$, —CONR$_6$R$_7$, —CH$_2$OH, —CH$_2$OR$_8$, —CHO, —SR$_8$, —SOR$_8$, —SO$_2$R$_8$, —SO$_3$H, —SO$_2$NR$_6$R$_7$, —OCH$_2$CH$_2$OCOR$_8$, —CH=NOH, —CH=NOR$_8$, —COR$_9$, —CH(OH)R$_9$, —CONHSO$_2$R$_8$, —CH(OR$_8$)$_2$, —NHCOOR$_8$, —CH=CHR$_{10}$, —OCONR$_6$R$_7$, —CH$_2$OCONR$_6$R$_7$, —CH$_2$CH$_2$OCONR$_6$R$_7$, or by 1,3-dioxolane or 1,3-dioxane which is optionally mono- or polysubstituted by methyl; or $R_2$ is a group
A—$C_1-C_6$-alkylene-, A—$C_2-C_6$-alkenylene, A—$C_2-C_6$-alkynylene, A—CONH—$C_1-C_6$-alkylene-, A—CONH—$C_2-C_6$-alkenylene- or A—CONH—$C_2-C_6$-alkynylene-, A—NHCO—$C_1-C_6$-alkylene, A—NHCO-$C_2-C_6$-alkenylene, A—NHCO—$C_2-C_6$-alkynylene, wherein A is a C- linked 5- or 6-, membered heterocyclic ring selected from the group consisting of tetrahydrofuran, tetrahydrofuranone, γ-butyrolactone, 2-pyran, γ-pyran, tetrahydropyran, pyrrole, pyrroline, pyrrolidine, piperazine, morpholine, thiomorpholine, imidazole, imidazoline, imidazolidine, pyrazole, pyrazoline, triazole, tetrazole, oxazole, oxadiazole, and pyrazolidine, wherein the heterocyclic ring may optionally be mono- or polysubstituted by $C_1-C_4$-alkyl, halogen, —OR$_8$, —CN, —NO$_2$, —NH$_2$, —OH, =O, —COOH, —SO$_3$H, —COOR$_8$, —CONR$_6$R$_7$, —COR$_9$, —SO$_2$—R$_8$, or $R_3$ is $C_3-C_7$-cycloalkyl, optionally substituted by =O, —OH, —OR$_8$, —OCOR$_8$, or $R_3$ is phenyl, which is optionally substituted by —OH, halogen, —OR$_8$, $C_1-C_4$-alkyl, —NH$_2$, —COOH, —SO$_3$H, —COOR$_8$, —OCH$_2$COOR$_8$, —CN, or —OCH$_2$CONR$_6$R$_7$, or $R_3$ is a norbornane-, norbornene-, adamantane-, noradamantane- or a $C_3-C_6$-dicycloalkylmethyl group; or $R_3$ is —CH=CH-phenyl, wherein the phenyl ring is mono- or polysubstituted by methoxy, hydroxy or halogen; or $R_3$ is a [3.3.0]-bicyclooctane; or $R_3$ is a C-linked piperidine or furan;

$R_4$ is a p-methoxybenzyl, 2,4-dimethoxybenzyl or 2,4,6-trimethoxybenzyl group;

$R_5$ is $C_1-C_4$-alkyl, optionally substituted by —OH, —OCOR$_8$, —NH$_2$, —NR$_6$R$_7$ or —NHCOR$_8$; or $R_5$ is —CH$_2$CH$_2$OH, —CH$_2$CH$_2$OCOR$_8$, —CH$_2$CH$_2$CH$_2$OH; or —CH$_2$CH$_2$CH$_2$OCOR$_8$;

$R_6$ is hydrogen, a $C_3-C_6$-cycloalkyl group, optionally substituted by $C_1-C_4$ alkyl, hydroxy or halogen, a branched or unbranched alkyl-, alkenyl- or alkynyl-group having up to 10 carbon atoms, which may optionally be substituted by hydroxy, phenyl, amino, or $C_1-C_8$-alkoxy; or $R_6$ is —(CH$_2$)$_m$—NHCOOR$_8$ (wherein m=1, 2, 3 or 4);

$R_7$ is hydrogen, a $C_3-C_6$-cycloalkyl group, optionally substituted by $C_1-C_4$ alkyl, hydroxy or halogen, a branched or unbranched alkyl-, alkenyl- or alkynyl-group having up to 10 carbon atoms, which may optionally be substituted by hydroxy, phenyl, amino, or $C_1-C_8$-alkoxy; or $R_7$ is —(CH$_2$)$_m$—NHCOOR$_8$ (wherein m=1, 2, 3 or 4);

or $R_6$ and $R_7$ together with the nitrogen atom form a saturated or unsaturated 5- or 6-membered heterocyclic ring selected from the group consisting of pyrrole, pyrroline, pyrrolidine, piperidine, piperazine, N-benzylpiperazine, morpholine, thiomorpholine, imidazole, imidazoline, imidazolidine, pyrazole, pyrazoline, and pyrazolidine wherein the hetrocyclic ring may be substituted by a branched or unbranched $C_{1-4}$-alkyl group, or may carry one of the following groups:
—(CH$_2$)$_n$—NH$_2$, —(CH$_2$)$_n$NH—$C_1-C_4$-alkyl, —(CH$_2$)$_n$—N($C_1-C_8$-alkyl)$_2$, or —(CH$_2$)$_n$—NHCOOR$_8$, (wherein n=2, 3 or 4), =O, halogen, —OR$_8$, —CN, —NO$_2$, —NH$_2$, —OH, —COOH, —SO$_3$H, —COOR$_8$, or —SO$_2$R$_8$;

$R_8$ is hydrogen, $C_1-C_4$-alkyl, $C_2-C_4$-alkenyl, $C_2-C_4$-alkynyl, or a benzyl- or phenyl-group, which is optionally mono- or polysubstituted by —OCH$_3$;

$R_9$ is $C_1-C_4$-alkyl, $C_2-C_4$-alkenyl, $C_2-C_4$-alkynyl, or, $C_3-C_6$-cycloalkyl;

$R_{10}$ is —COOR$_8$, —CH$_2$OR$_8$, —CONR$_6$R$_7$, hydrogen, $C_1-C_3$-alkyl, or —CH$_2$NR$_6$R$_7$;

$R_{11}$ is hydrogen, phenyl, —CH$_3$;

optionally in the form of the racemates, the enantiomers, the diastereomers and the mixtures thereof and optionally in the form of the pharmacologically acceptable salts thereof.

9. The compound recited in claim 1, wherein $R_3$ is a group selected from the following:

-continued

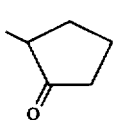 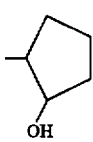 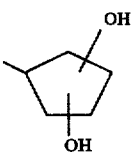

and $R_2$ is —$CH_2CH_2OH$, —$CH_2CH_2OCOCH_3$, —$(CH_2)_3OCOCH_3$, —$(CH_2)_3OCH_3$, —$CH_2CH_2COCH_3$, —$CH_2CH_2CH(OH)CH_3$, —$CH_2CH_2COOCH_3$, —$CH_2CH_2CONH_2$; —$(CH_2)_3CONH_2$, —$CH_2CH=NOH$, —$(CH_2)_3CN$, —$CH_2CH_2SCH_2CH_3$, —$CH_2CH_2SCH_2CH_2OH$, —$CH_2CH_2SO_2CH_2CH_2OH$, —$CH_2CH_2SO_2CH_2CH_2OCOCH_3$, A—$(CH_2)_2$— or A—$(CH_2)_3$—, wherein A is a C- linked 5- or 6-.membered heterocyclic ring selected from the group consisting of tetrahydrofuran, γ-butyrolactone, 2-pyran, γ-pyran, tetrahydropyran, pyrrole, pyrroline, pyrrolidine, piperazine, morpholine, thiomorpholine, imidazole, imidazoline, imidazolidine, pyrazole, pyrazoline, triazole, tetrazole, oxazole, oxadiazole, and pyrazolidine, wherein the heterocyclic ring may optionally be mono- or polysubstituted by $C_1$-$C_4$-alkyl, halogen, —$OR_8$, —CN, —$NO_2$, —$NH_2$, —$CH_2NR_6R_7$, —OH, =O, —COOH, —$SO_3H$, —$COOR_8$, $CONR_6R_7$, —$COR_9$, —$SO_2$—$R_8$, —$CONR_6R_7$ or

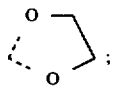

optionally in the form of the racemates, the enantiomers, the diastereomers and the mixtures thereof and optionally the pharmacologically acceptable salts thereof.

* * * * *